(12) United States Patent
Singh et al.

(10) Patent No.: US 11,734,822 B2
(45) Date of Patent: Aug. 22, 2023

(54) SYSTEM AND METHOD FOR AUTOMATED GAMETE SELECTION

(71) Applicant: Thread Robotics Inc., San Jose, CA (US)

(72) Inventors: Gurjeet Singh, San Jose, CA (US); Kiran Joshi, San Jose, CA (US); Sahil Gupta, San Jose, CA (US)

(73) Assignee: Thread Robotics Inc., San Jose, CA (US)

( * ) Notice: Subject to any disclaimer, the term of this patent is extended or adjusted under 35 U.S.C. 154(b) by 0 days.

(21) Appl. No.: 17/871,665

(22) Filed: Jul. 22, 2022

(65) Prior Publication Data

US 2022/0358653 A1 Nov. 10, 2022

Related U.S. Application Data

(63) Continuation of application No. 17/690,910, filed on Mar. 9, 2022, now Pat. No. 11,481,900.

(Continued)

(51) Int. Cl.
| | |
|---|---|
| *G06T 7/00* | (2017.01) |
| *G06V 20/69* | (2022.01) |
| *G06T 7/20* | (2017.01) |
| *G06V 20/40* | (2022.01) |
| *G16B 40/00* | (2019.01) |
| *G16B 5/20* | (2019.01) |

(Continued)

(52) U.S. Cl.
CPC .............. *G06T 7/0012* (2013.01); *G06T 7/20* (2013.01); *G06V 10/764* (2022.01); *G06V 20/46* (2022.01); *G06V 20/69* (2022.01); *G16B 5/20* (2019.02); *G16B 40/00* (2019.02); *G06T 2207/30024* (2013.01); *G16B 50/10* (2019.02)

(58) Field of Classification Search
CPC ........ G06T 7/0012; G06T 2207/30024; G06V 10/764; G06V 20/69; G06V 20/698; A61B 5/43; G01N 2021/0181; G01N 2021/1765; G01N 2021/177
See application file for complete search history.

(56) References Cited

U.S. PATENT DOCUMENTS

| | | |
|---|---|---|
| 10,977,477 B2 | 4/2021 | Shafiee |
| 2006/0257909 A1 | 11/2006 | Harton et al. |

(Continued)

FOREIGN PATENT DOCUMENTS

| | | |
|---|---|---|
| WO | 2015153691 A2 | 10/2015 |
| WO | 2020090947 A1 | 5/2020 |

(Continued)

OTHER PUBLICATIONS

"Machine translation of WO2020090947A1", via Google Patents, 38 pages. (Year:2022).

(Continued)

*Primary Examiner* — Andrew W Johns
(74) *Attorney, Agent, or Firm* — Jeffrey Schox; Diana Lin

(57) ABSTRACT

In variants, a method for automated gamete selection can include: sampling a video of a scene having a plurality of gametes, tracking each gamete across successive images, and determining attribute values for a gamete, and selecting the gamete. The attribute values can be determined using a model trained to predict the attribute values for the gamete based on a video.

5 Claims, 18 Drawing Sheets

Related U.S. Application Data

(60) Provisional application No. 63/176,113, filed on Apr. 16, 2021, provisional application No. 63/158,773, filed on Mar. 9, 2021.

(51) Int. Cl.
*G06V 10/764* (2022.01)
*G16B 50/10* (2019.01)

(56) References Cited

U.S. PATENT DOCUMENTS

| | | | |
|---|---|---|---|
| 2017/0089820 | A1 | 3/2017 | Wong et al. |
| 2017/0091926 | A1* | 3/2017 | Kinukawa et al. .. G01N 33/689 |
| 2017/0109879 | A1 | 4/2017 | Urbano et al. |
| 2018/0330510 | A1 | 11/2018 | Watanabe |
| 2018/0348114 | A1 | 12/2018 | Hsu et al. |
| 2019/0120750 | A1 | 4/2019 | Kim |
| 2019/0302093 | A1 | 10/2019 | Hsu et al. |
| 2020/0226750 | A1 | 7/2020 | Shafiee et al. |
| 2020/0311916 | A1 | 10/2020 | Tran |
| 2021/0319208 | A1 | 10/2021 | Ohara et al. |
| 2021/0374952 | A1* | 12/2021 | Shafiee et al. ......... C12M 41/46 |
| 2022/0156922 | A1* | 5/2022 | Chévez Badiola ... G06T 7/0012 |
| 2023/0061402 | A1* | 3/2023 | Cassuto et al. ....... G06T 7/0014 |

FOREIGN PATENT DOCUMENTS

| | | |
|---|---|---|
| WO | 2020198779 A1 | 10/2020 |
| WO | 2021200003 A1 | 10/2021 |

OTHER PUBLICATIONS

"Machine translation of WO2021200003", via Google Patents, 20 pages (Year:2022).

"Priority document JP2020-063284 to WO2021/20003A1", issued Mar. 25, 2021, 41 pages.

"WHO laboratory manual for the Examination and processing of hum semen Fifth Edition", World Health Organization Jun. 2021.

Ben-Yehuda, Keren, et al., "Simultaneous Morphology, Motility and Fragmentation Analysis of Live Individual Sperm Cells for Male Fertility Evaluation", Advanced Intelligent Systems, vol. 4, Issue 4, 12 pages, Dec. 26, 2021, https://onlinelibrary.wiley.com/doi/10.1002/aisy.202100200.

Butola, Ankit, et al., "High Spatially sensitive quantitative phase imaging assisted with deep neural network for classification of human spermatozoa under stressed condition", Scientific Reports, Aug. 4, 2020, vol. 10, 12 pages.

Chang, Violeta, et al., "Gold-standard for computer-assisted morphological sperm analysis", Computers in Biology and Medicine, Apr. 1, 2017, vol. 83, pp. 143-150.

Dai, Changsheng, et al., "Automated motility and morphology measurement of live spermatozoa", American Society of Andrology and European Academy of Andrology, 2021;00:1-9.

Leung, Clement, "Robotic Single Cell Manipulation for Biological and Clinical Applications", Thesis, 2011, University of Toronto, 98 pages, https:www.bac-lac.gc.ca/eng/services/thesis/Pages/item.aspx?idNumber=1032903771.

McCallum, Christopher, et al., "Deep learning-based selection of human sperm with high DNA integrity", Communications Biology (2019)2:250.

Valiuskaite, Viktorija, et al., "Deep Learning Based Evaluation of Spermatozoid Motility for Artificial Insemination", Sensors 2021, 21, 72.

Wang, Yihe, et al., "Prediction of DNA Integrity from Morphological Parameters Using a Single-Sperm DNA Fragmentation Index Assay", Adv. Sci. 2019, 6, 1900712.

You, Jae Bem, et al., "Machine learning for sperm selection", Nature Review Urology vol. 18, Jul. 2021.

Yuzkat, Mecit, et al., "Multi-model CNN fusion for sperm morphology analysis", Computers in Biology and Medicine, vol. 137, 12 pages, Aug. 24, 2021.

\* cited by examiner

SYSTEM AND METHOD FOR AUTOMATED GAMETE SELECTION

CROSS-REFERENCE TO RELATED APPLICATIONS

This application is a continuation of U.S. application Ser. No. 17/690,910 filed 9 Mar. 2022, which claims the benefit of U.S. Provisional Application No. 63/158,773 filed 9 Mar. 2021 and U.S. Provisional Application No. 63/176,113 filed 16 Apr. 2021, each of which is incorporated in its entirety by this reference.

TECHNICAL FIELD

This invention relates generally to the fertility field, and more specifically to a new and useful automated gamete selection method in the fertility field.

BACKGROUND

Traditionally, gamete selection for in vitro fertilization (IVF) is performed by medical professionals (e.g., embryologists, andrologists, etc.) that have extensive domain experience. Unfortunately, the quality of gamete selection directly influences the success rate of the IVF, and gamete selection quality can vary drastically across different medical professionals. Furthermore, because the professionals must analyze gametes one at a time, conventional gamete selection methods have very low throughput, and force professionals to only consider a small proportion of the total possible candidates (e.g., 50 gametes out of 100 million candidates in a sample). This lowers the probability that a high quality gamete will be considered, much less selected, for future IVF processes. Furthermore, low-fertility samples may have few or no high-quality gametes, and conventional systems lack the ability to select between gametes that are defective in different ways.

Conventional systems do not incorporate models that ingest information from a gamete population to perform an individual gamete selection (e.g., relative to the gamete population). In particular, conventional methods lack the ability to determine a distribution of gametes in a sample, wherein the best gamete in the population can be selected based on its position in the distribution. Nor do conventional methods have a means of sequentially picking the next best gamete based on the population distribution. Rather, if a gamete selection is found to be non-ideal (e.g., an abnormal gamete), professionals must manually re-analyze the sample of gametes to find a new selection.

Thus, there is a need in the fertility field to create a new and useful gamete characterization and/or selection method. This invention provides such a new and useful method.

DETAILED DESCRIPTION

The following description of the embodiments of the invention is not intended to limit the invention to these embodiments, but rather to enable any person skilled in the art to make and use this invention.

1. Overview

Figure 1:
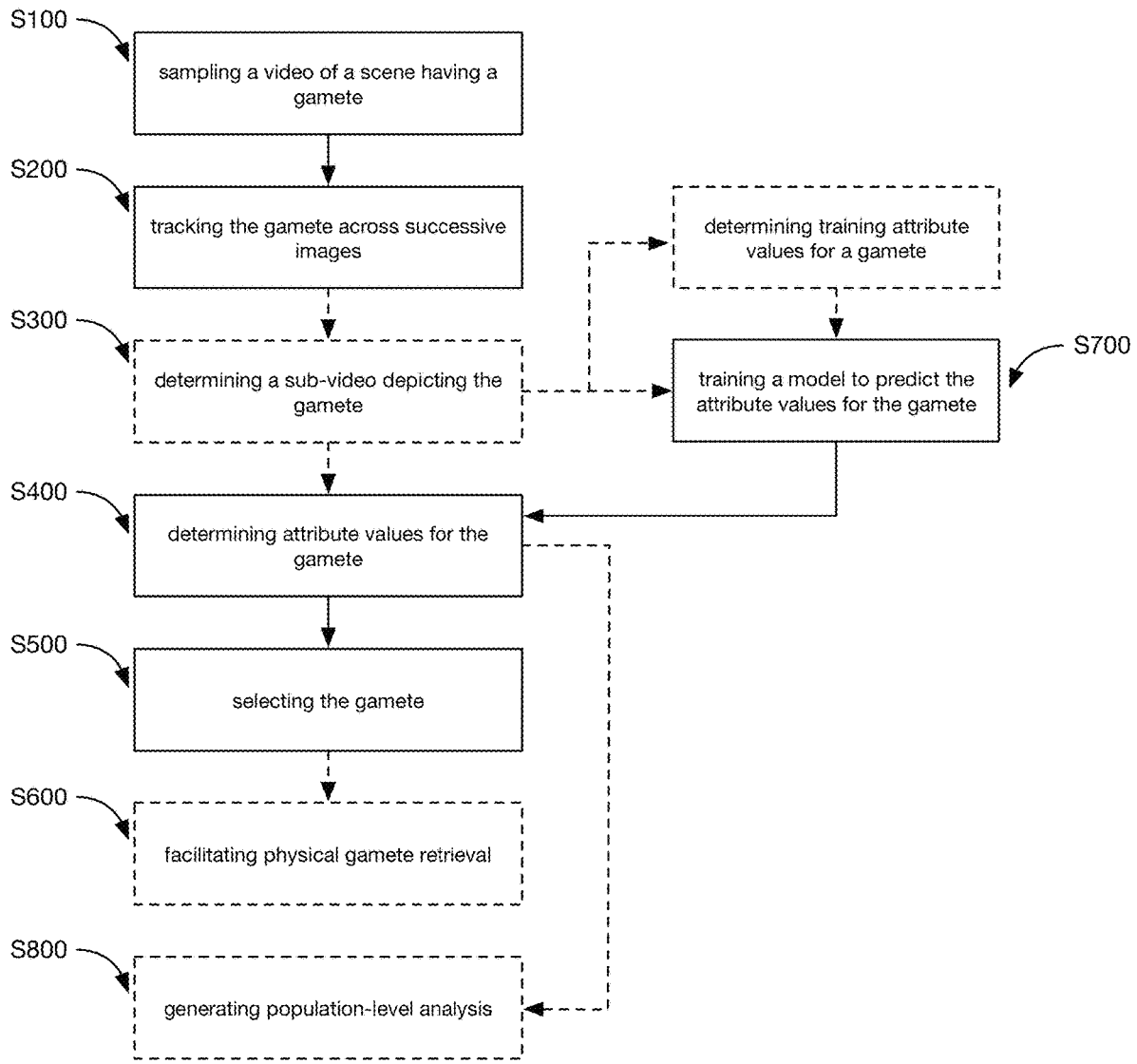
FIG. 1 is a schematic representation of a variant of the method.

As shown in FIG. 1, variants of the automated gamete selection method include: sampling a video of a scene having a gamete S100, tracking the gamete across successive images S200, determining attribute values for the gamete S400, and selecting the gamete S500. The method can additionally or alternatively include training a model to predict the attribute values for the gamete S700.

The method can function to automatically analyze, identify, and optionally select gametes with a high probability of IVF success. In variants, the method can function to generate a model that can infer attribute values (e.g., destructive attribute values) from noninvasive measurements of a gamete.

2. Examples

In an example, the method for gamete selection can include: sampling a video of gametes from a gamete population (e.g., of a gamete sample, on a microscope slide); identifying individual gametes within the video; tracking each identified gamete; optionally generating a set of sub-videos of each identified gamete (e.g., a series of clips spanning an evaluation epoch, such as a series of 6-second clips); determining attribute values for each identified gamete based on each sub-video of the respective sub-video set using a set of trained gamete attribute models (e.g., determining a set of attribute values for each gamete for each evaluation epoch); and selecting the gamete based on the attribute values determined from the gamete's sub-videos. In a specific example, selecting the gamete can include: aggregating the attribute values for each gamete from each sub-video (and/or epoch) into a distribution (e.g., a distribution of scores, a distribution of values, etc.), and selecting the gamete based on the aggregated values. For example, the gamete can be selected based on: the distribution spread, the distribution mean, the confidence score, and/or any other suitable measure of the aggregated or individual attribute values. The selected gamete can be: a high-quality gamete (e.g., mean or mode or confidence score above a threshold, lowest spread, etc.), an uncertain gamete (e.g., a confidence score less than a threshold, etc.), and/or any other gamete.

The gamete attribute values can represent: a gamete's viability for successful fertilization and/or survival to blastocyst stage and/or blastocyst euploid probability and/or pregnancy and/or live birth, a probability of selection by a specialist, a specialist label of the gamete, a degree of healthiness and/or normality (e.g., relative to a reference gamete population), a morphology parameter (e.g., quantitative rating, qualitative classification, etc.), a motility parameter (e.g., quantitative rating, qualitative classification, etc.), a gamete measurement (e.g., destructive information), post-fertilization development data, and/or any other selection metric. A gamete can be selected for: retrieval (e.g., select the most viable or highest-quality gamete(s) for assistive reproductive processes, select gametes satisfying selection criterion, etc.), model training/feedback (e.g., to be manually scored by a specialist), secondary labelling (e.g., gametes with uncertain attribute values are sent to a specialist for value confirmation and/or manual labelling), additional attribute value determination (e.g., where a first attribute value determined using a first model filters the gametes prior to determination of a second attribute value using a second model), and/or any other gamete use. In variants, attribute value determination and/or selection can be performed in real- or near-real time, while the gamete is within the population (e.g., on the microscope slide).

The attribute value model(s) can be trained to predict a specialist-assigned attribute value and/or extract a computational attribute value for individual gametes based on the gamete's sub-video and/or a source video (that the sub-videos were generated from). The specialist-assigned attribute values can be assigned by a single specialist or by multiple specialists, wherein the attribute values assigned by different specialists can be averaged, summed, normalized, or otherwise aggregated. For example, a selection probability can be determined for the gamete based on multiple specialist-assigned attribute values, where the gamete attribute model can be trained to predict the selection probability.

However, the gametes can be otherwise selected.

3. Technical Advantages

Variants of the technology can confer one or more advantages over conventional technologies.

First, the technology can drastically increase throughput (e.g., from tens of analyzed gametes per patient to thousands, tens of thousands, hundreds of thousands, and/or millions of analyzed gametes per patient), by enabling real-time, concurrent, non-destructive analysis of multiple live gametes. For example, the technology can increase the number of candidate gametes that are considered (e.g., analyzed, sampled) per gamete selected. In another example, the technology can increase the number of gametes selected per unit time.

Second, the inventors have discovered that the qualitative aspects of some features (e.g., motion features) are more important than the quantitative aspects of said features. For example, how a gamete is moving (e.g., linear progressivity) can be more indicative of gamete quality than the kinematics of gamete motion. This technology enables both the quantitative power of machine learning models and the qualitative expertise of skilled specialists to be used by training one or more gamete attribute models (e.g., gamete selection or classification models) using expert selections and/or classifications. This can increase the IVF-ICSI success rate, particularly when high-success-rate specialists are used to generate gamete attribute values for model training. In a first example, gamete selection criteria (e.g., heuristics) can be learned or specified from historic specialist gamete selections. In a second example, qualitative classifiers that output qualitative labels about the gamete and/or portions thereof can be trained on gamete images, videos, or other data labeled by the specialist. In a third example, a gamete attribute model can be trained based on attribute values extracted from images of the plurality of gametes and the gametes eventually selected by the specialists (e.g., during manual gamete selection).

Third, variants of the technology can split the selection process into different analysis stages (e.g., feature extraction, parameter determination, and scoring) instead of using an end-to-end model (such as a neural network, a model with learned weights, etc.) to select the gamete. This can provide increased auditability and explainability (e.g., for certification purposes).

Fourth, low-fertility samples may have low or no high-viability gametes (e.g., no normal gametes). In these situations, methods that select gametes based on a strict set of morphological and/or motility criterion (e.g., only select gametes that meet the WHO description for "normal" gametes) will not be able to select candidate gametes, since little to no gametes would satisfy the criterion, and since the methods are unable to select between differently-defective gametes. In contrast, variants of this technology can still select gametes by relying on specialist selection predictions (e.g., wherein differently-defective gametes are selected by specialists for ART usage), population-level comparisons (e.g., select the "best" gametes, the gametes with the highest probability of selection, etc.), and/or other datum.

Fifth, model uncertainty can result in inaccurate gamete attribute value outputs and/or selection of less optimal gametes. Variants of the technology can mitigate gamete selection errors and/or generate more accurate training data. In a first example, the technology can select gametes associated with high model uncertainty (e.g., to filter out high uncertainty gametes, to select high-uncertainty gametes for manual labeling and/or selection for model feedback, etc.). In a second example, the technology can select gametes with low uncertainty (e.g., for gamete retrieval).

However, further advantages can be provided by the system and method disclosed herein.

4. System

Figure 2:
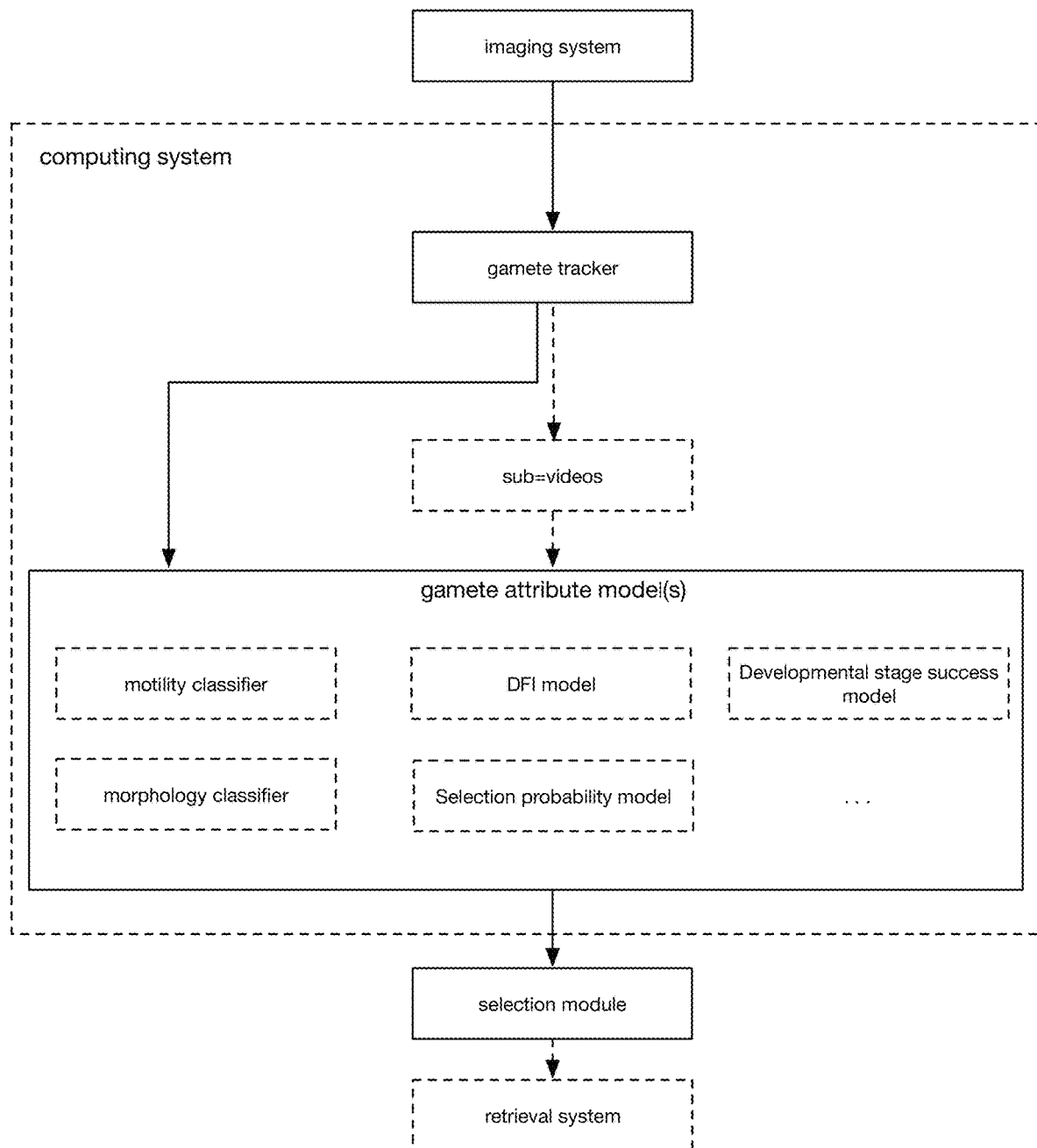
FIG. 2 is a schematic representation of an example of the system.

The automated gamete selection method can be performed using a system including one or more: imaging systems, tracking systems, selection systems, computing systems, retrieval systems, measurement systems, specialist sets, and/or any other suitable system. An example of the system is shown in FIG. 2.

Figure 15:
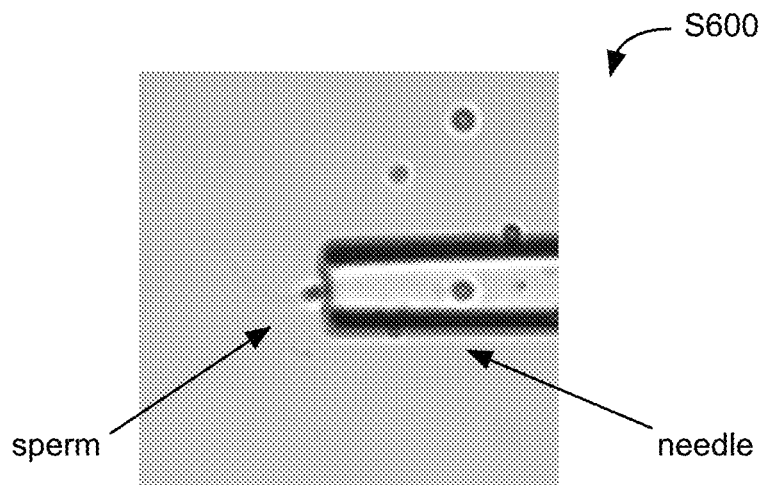
FIG. 15 depicts an illustrative example of aspirating a spermatozoon.

The imaging system is preferably an optical microscopy system, but can be any other suitable system. The imaging system can include a bright-field microscope, confocal microscope, phase contrast microscope, DIC microscope, and/or any other microscope. The imaging system can include one or more cameras (e.g., monocular cameras, stereo cameras, CCD cameras, CMOS cameras, multi- or hyper-spectral cameras, etc.). The camera can be modified to interface with a microscope. The camera resolution is preferably selected such that each gamete is represented by at least 50 px, 75 px, 100 px, and/or 150 px, a range or value therein, but can alternatively be higher or lower. The resolution of the resultant image can be: 4 Mpixels, 8 Mpixels, 12 Mpixels, 16 Mpixels, 24 Mpixels, 36 Mpixels, 44 Mpixels, and/or have another resolution. The imaging system field of view can be: larger, smaller, equal to, and/or otherwise related to the extent of the scene. The scene can be defined by a slide, petri dish, tray, well, vial, container, workspace, and/or other gamete repository. The imaging system can acquire images at 10, 15, 20, 25, 30, 35, 40, 50, 60, 70, 80, 90, 100 frames per second, any range therein, and/or any other frame rate suitable for the gametes (e.g., moving at approximately 25 microns per second). Data acquired by the imaging system can be downsampled (e.g., downsampling the frame resolution for input to the tracking system, downsampling the framerate for morphology attribute value determination, etc.), stitched (e.g., to form a larger frame), cropped (e.g., from full-frame to partial-frame), and/or otherwise processed The retrieval system can function to facilitate physical isolation and/or retrieval of a selected gamete for downstream use (e.g., measurements, attribute value determination, gamete transfer, IVF processes, etc.). In examples, the retrieval system can function to immobilize a gamete, move (e.g., translate and/or rotate) a gamete, aspirate a gamete, transfer a gamete to a target location, otherwise isolate a gamete from a set of gametes, and/or otherwise manipulate one or more gametes. The retrieval system can include an intracytoplasmic sperm injection (ICSI) or intracytoplasmic morphologically selected sperm injection (IMSI) needle and/or micropipette, a blade, an aspirator, a laser, suction end effector, cell sorting devices (e.g., microfluidic cell sorter, a microfluidic chip, etc.), optical tweezers, and/or any other isolation, immobilization, or retrieval device. An aspirator can be a standard micromanipulation needle (e.g., micropipette), a micromanipulation needle with a larger than standard bore (e.g., a needle with a 17-18 micrometer bore, to minimize damage to the gamete; example shown in FIG. 15), and/or any other suitable needle and/or aspirator.

The retrieval system can be mounted on the imaging system (e.g., on the microscope stage), on a separate platform, in the microscope (e.g., a laser connected to the objective lens), on a robotic arm, and/or be otherwise configured relative to the imaging system and/or any other system or module. The retrieval system can be automatically actuated, manually actuated, or stationary. Actuation of the retrieval system can occur in any number of dimensions.

The tracking system can function to identify and/or track gametes across video frames. Gametes can be tracked across time (e.g., across successive frames of a video) and/or spatially (e.g., in physical space across the scene). The tracking system is preferably digital, but can additionally or alternatively be physical (e.g., physically move the camera and/or stage to keep the gamete in the field of view). The tracking system can include one or more models (e.g., gamete detection models, tracking models, motion models, appearance models, feature extraction models, etc.), a computing system (e.g., local or remote from the imaging system), and/or any other suitable system or module. Optionally, one or more components of the imaging system and/or scene can be actuated based on the tracking system output (e.g., based on a gamete track). In a first example, the camera and/or scene can be actuated in the z-direction to maintain focus on a target gamete. In a second example, the camera and/or scene can be actuated in the x- and/or y-directions to spatially track a gamete across the scene (e.g., when the field of view is less than the scene size), ensuring the gamete remains within the field of view and/or at the center of the field of view.

The selection system can function to analyze gametes (e.g., determine attribute values for a gamete) and/or select a gamete from a set (e.g., based on the attribute values). The selection system can include one or more models (e.g., gamete attribute models, selection models, etc.), a computing system, one or more specialists, and/or any other suitable system or module. The gamete attribute models and/or selection models are preferably biased toward resulting in little or no false positive gamete selections (e.g., where a nonviable gamete is selected), but can be biased to have little or no false negative gamete selections, or be otherwise trained. The selection system can be local (e.g., collocated in the same facility) and/or remote (e.g., be a cloud-based system) to the imaging system and/or the retrieval system. In an illustrative example, a video can be sampled at the imaging system and then transmitted to the selection system. The selection system can then identify a gamete for selection and transmit the selection to the retrieval system for gamete retrieval.

Models in the system (e.g., gamete detection model, tracking model, motion model, appearance model, feature extraction model, gamete attribute model, selection model, etc.) can leverage classical or traditional approaches (e.g., models with manually coded parameters; models using manually-selected feature descriptors, such as SIFT, SURF, FAST, Hough transforms, geometric hashing, etc. paired with an SVN, k-nearest neighbors, and/or other classifiers; models that are entirely or partially manually defined; etc.), leverage machine learning approaches (e.g., have learned parameters), and/or be otherwise constructed. Each model can use one or more of: regression, classification (e.g., a multiclass classifier, a binary classifier, etc.), clustering, neural networks (e.g., CNNs, DNNs, etc.), rules, heuristics, equations (e.g., weighted equations, etc.), instance-based methods (e.g., nearest neighbor), regularization methods (e.g., ridge regression), decision trees, random forest, Bayesian methods (e.g., Naïve Bayes, Markov), kernel methods, probability, deterministics, genetic programs, generative models, support vectors, and/or any other suitable method. The models can be learned (e.g., using supervised learning, self supervised learning, unsupervised learning, transfer learning, etc.), fit, trained, predetermined, and/or can be otherwise determined. Models can be trained to predict specialist labels using data from the specialist set (e.g., labeled gametes, labeled gamete videos and/or sub-videos, labeled gamete images, etc.), trained or programmed to calculate a qualitative attribute (e.g., the neck angle, head sphericality, linear progressivity, etc.), and/or otherwise generated. Models can be trained once, iteratively trained (e.g., as more training data is generated by the method), and/or trained or retrained any number of times.

The computing system can include one or more: CPUs, GPUs, custom FPGA/ASICS, microprocessors, servers, cloud computing, and/or any other suitable components. The computing system can be local, remote, distributed, or otherwise arranged relative to the imaging system and/or any other system or module.

The set of specialists (e.g., specialist panel) can include a group of one or more embryologists, reproductive endocrinologists, andrologists, and/or any other specialists. The specialists can label images and/or videos (e.g., sub-videos) of one or more gametes, select gametes for assistive reproductive technologies (ART), and/or perform other functionalities. In an example, the specialists can label gametes based on a World Health Organization (WHO) gamete classification system, and/or use any other taxonomy. The labels can include attribute values, gamete bounding boxes, and/or any other label.

Measurement systems can include one or more tools for assays (e.g., to measure information for a gamete, an embryo, a fetus, etc.). The assays can measure: DNA fragmentation (DFI), vitality, antibody coatings, morphology, electro dynamical measurements, preimplantation genetic testing (PGT), prenatal testing, and/or any other gamete attribute that can be experimentally measured. Example assays and techniques for DNA fragmentation index (DFI) measurement include: the acridine orange test (AO), sperm chromatin structure assay (SCSA), deoxynucleotidyl transferase-mediated dUTP nick end labeling assay (TUNEL) (e.g., by flow cytometry or light microscopy), the single-cell gel electrophoresis assay (COMET), the sperm chromatin dispersion test (SCD, e.g., Halosperm™), flow cytometry, polymerase chain reaction (PCR), and/or other DFI methods. Example assays and techniques for vitality testing include: eosin-nigrosine, eosin, hypo-osmotic swelling, and/or any other assay. Example assays and techniques for antibody coating assessment can include: mixed antiglobulin reaction tests, direct immunobead tests, indirect immunobead tests, and/or any other antibody test. Examples assays and techniques for morphology assessment can include: fixation and sequential staining, Papanicolaou staining, Shorr staining, rapid staining, and/or any other morphology method. Example assays and techniques for preimplantation genetic testing (PGT) include: fluorescence in situ hybridization (FISH), PCR, array-based comparative genomic hybridization (aCGH), next-generation sequencing (NGS), single nucleotide polymorphism (SNP) array, whole genome amplification (WGA), and/or other PGT methods (e.g., including methods for preimplantation genetic testing-aneuploidy, preimplantation genetic testing-monogenic, preimplantation genetic testing-structural rearrangements, etc.). Example assays and techniques for prenatal testing include: chorionic villus sampling, amniocentesis, and/or any other prenatal testing methods.

However, the system can include any other suitable components.

5. Method

As shown in FIG. 1, variants of the automated gamete selection method include: sampling a video of a scene having a gamete S100, tracking the gamete across successive images S200, determining attribute values for the gamete S400, and selecting the gamete S500. The method can optionally include training a model to predict the attribute values for the gamete S700. The method functions to select a gamete. The gamete (and/or associated data) can be used: for assistive reproductive technologies (ART), to generate training data, and/or otherwise used.

All or portions of the method can be performed for a single gamete (e.g., individually isolated using a microfluidic isolation system, etc.) and/or for a set of gametes (e.g., a plurality of gametes, from one or more gamete samples from the same or different patient). All or portions of the method can be performed once for each gamete, iteratively for each gamete in the set, once for the gamete set, iteratively for each gamete set, and/or performed any other number of times.

Different instances of the method can be concurrently or contemporaneously performed for different gametes in the same (or different) sample; alternatively, different method instances for different gametes can be performed asynchronously (e.g., sequentially). In a first example, the method can be contemporaneously executed for all gametes in a frame. In a variant of this example, the selected gamete can be tracked through the scene, and the method repeated for the gamete and new adjacent gametes appearing in the field of view. In a second example, the method can be executed for each gamete serially, such that gametes are analyzed one at a time. However, any other number of method instances can be concurrently or asynchronously executed.

The set of gametes can be selected from a population of gametes in a sample (e.g., selected via S500), include all gametes in an image and/or field of view, include all gametes in a sample, include all gametes in a scene, be a subset thereof, and/or be otherwise defined.

The gametes can be mobile or static. Examples of the gametes include: spermatozoa, ovum, and/or other gametes. The gametes can be: human gametes, animal gametes (e.g., mouse, bovine, porcine, fowl, etc.), and/or from other animals. All or portions of the method can be performed in real- or near-real time (e.g., S100-S600, etc.), but can alternatively be performed asynchronously or at any other suitable time.

All or portions of the method can be performed using one or more components of the system, using a computing system, by a user, and/or by any other suitable system. All or portions of the method can be performed automatically, manually, semi-automatically, and/or be otherwise performed.

Sampling a video of a scene having a gamete S100 can function to obtain sensor measurements of one or more gametes. S100 is preferably performed by the imaging system, but can be performed by another system. S100 can be performed continuously, periodically, iteratively (e.g., for a set of gametes, for a set of time periods, etc.), in response to a trigger, and/or at any other frequency. S100 can be performed before selecting a gamete S500 (e.g., where the video is used for gamete selection), after selecting a gamete S500 (e.g., where the video is sampled for one or more selected gametes), during one or more of S200-S500, and/or at any other suitable time.

Figure 7:
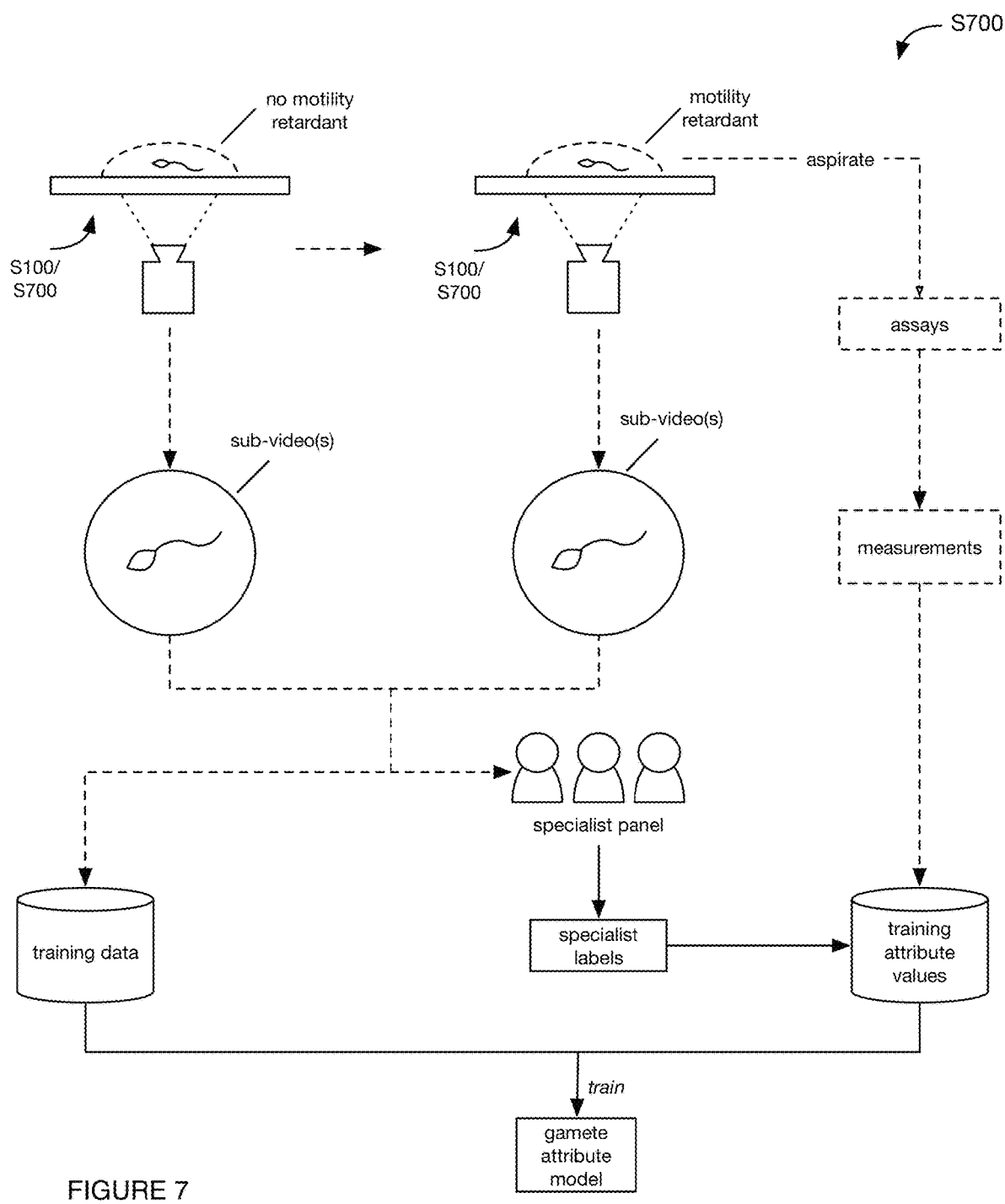
FIG. 7 depicts an example of training a gamete attribute model.

The gamete can be isolated (e.g., via S600, using the retrieval system) and/or not isolated from a population of gametes. The gamete can be in a prepared sample (e.g., to slow gamete motility, to dilute gamete concentration, etc.), an unprepared sample, and/or other sample. In a first variant, the sample can be prepared using a motility retardant, such as: polyvinylpyrrolidone (PVP), hyaluronate-containing products, mucus substitutes, viscous liquids, and/or other motility retardants. In a second variant, the sample can include seminal fluid (e.g., diluted and/or undiluted). The seminal fluid is preferably from the same donor as the sample gametes, but alternatively can be from one or more different donors. In a third variant, the sample can be prepared using a culture media. In a fourth variant, the sample can be unprepared. An example is shown in FIG. 7. However, the sample can be otherwise prepared.

The scene (e.g., slide, petri dish, tray, well, vial, container, workspace, etc.) is preferably configured such that the gametes lie in a single layer, but can alternatively be sized such that gametes overlap each other. The scene can be static or mobile. In the latter variant, the scene can optionally be connected to a stage (e.g., x-y stage, x-y-z stage, rotary stage, etc.), which functions to actuate the scene (e.g., along an x-, y-, and/or z-axis).

S100 preferably includes sampling a timeseries of images (e.g., video, sub-video, series of video frames), but can additionally or alternatively include sampling a single image (e.g., still image), sampling depth or height information (e.g., by focusing on different focal planes, by changing the slide height, by using a depth sensor, etc.), and/or other images. The video focus can be static, where the imaging system camera does not move relative to the scene (e.g., where a single region of the overall scene is sampled). Alternatively, the video focus can be dynamic, where the imaging system camera moves relative to the scene (e.g., where various regions of the overall scene can be sampled).

The image (e.g., still image or video frame) can be a 2D image (e.g., RGB image, multispectral image, hyperspectral image, etc.), a 3D image (e.g., stereoimage, time of flight image, projected light image, depth measurement, point cloud, etc.). The image can be: a sub-image associated with a subregion of the overall scene, an image that encompasses the entire scene, an image that encompasses a majority of the scene, and/or an image that encompasses any other suitable portion of the scene. When the image is a sub-image, the sub-image can be: cropped from a full-frame image; sampled (e.g., contemporaneously, concurrently, asynchronously) with other sub-images (e.g., by the same or different imaging systems), but can be otherwise determined.

However, the video can be otherwise determined.

Tracking the gamete across successive images S200 can function to identify the same gamete instance across images, such that gamete features and/or attribute values extracted from different images can be associated with the same gamete. S200 can optionally be used to determine gamete-associated image segments (e.g., sub-video frames in S300). S200 can be performed after S100, after S300, during one or more of S100-S500, and/or at any other time. S200 can be performed for: one gamete at a time, multiple gametes at a time, and/or any other number of gametes.

The tracked gamete can be: all visible gametes (e.g., within the imaging system's field of view), a randomly-selected gamete, one or more gametes selected using a set of criteria (e.g., motion above a threshold level, motion having a target pattern, morphology having a certain set of features, size above a threshold size, etc.), one or more gametes selected in S500, and/or any other gamete.

The gamete can be digitally tracked (e.g., tracked across sequential images, with or without moving the imaging system relative to the physical scene), physically tracked (e.g., by moving the imaging system relative to the physical scene), and/or otherwise tracked.

S200 can be performed per image (e.g., on the full image of each image, a mosaiced super-image of the scene generated from different sub-images, a subportion of the image, etc.), on the video (e.g., a series of images, the video from S100, the sub-video from S300, etc.), and/or for any other set of images. S200 can be performed using the 2D image, 3D data, and/or any other data. The gamete can be tracked across consecutive images, nonconsecutive images, and/or any set of images. The gamete can be tracked: within a scene subregion (e.g., coextensive with the imaging system's field of view), only within the scene subregion depicted within the imaging system's field of view, across all or a portion of the scene, and/or across any other physical region. The gamete is preferably tracked using gamete features (e.g., appearance features, motion features, location, etc.), but can be tracked based on the images (e.g., sliding window of video frames, all images, image segments, etc.), a predicted gamete location, and/or any other suitable information. As used herein, features preferably refer to low-level features extracted from the raw data (e.g., computer vision features, such as edges, blobs, corners, gradients, etc.; timeseries features, such as amplitude, frequency, energy, etc.), but can additionally or alternatively refer to attributes and/or other information extractable from the raw data. The features can be extracted by autoencoders, (e.g., variational, denoising, convolutional, sparse, etc.), t-distributed stochastic neighbor embedding (t-SNE), uniform manifold approximation and projection (UMAP), locally linear embedding (LLE), linear discriminant analysis (LDA), independent component analysis (ICA), principal component analysis (PCA), and/or any other suitable feature extraction algorithm.

The gamete can be tracked using: object detection methods (e.g., using a trained gamete detector, using a shape-fitting model, etc.), object tracking and localization models, optical flow (e.g., phase correlation; block-based methods; differential methods, such as Lucas-Kanade, Horn-Schnuck, Buxton-Buxton, Black-Jepson, and/or variational methods; discrete optimization methods; etc.), other tracking modules (e.g., gamete trackers), and/or any other tracking method. The gamete can be tracked using: traditional computer vision methods (e.g., with hand-selected features, hand-coded relationships, etc.), deep learning methods (e.g., with learned features, learned weights, etc.), and/or any other method or model. The gamete tracking models can be trained using: specialist-labelled images (e.g., that label image regions as depicting gametes); and/or otherwise trained. Over the course of the video, S200 can output: a track or tracklet for the gamete (e.g., timeseries of locations, positions, bounding box positions, or occupied pixels); kinematics; and/or other information. The track can subsequently be used to generate gamete sub-videos, determine motility attribute values, and/or otherwise used. The track can be 2D (e.g., 2D positions over time); 3D (e.g., 3D positions over time); and/or have any other suitable set of dimensions. The track can be generated from: the video, a sub-video, a series of sub-videos, a sliding window of video frames, all video frames, a single image, and/or from any other data. Each track can be associated with a gamete identifier (e.g., for the tracked gamete).

The gamete tracking models can track the gamete across images (e.g., cross-correlated across images) based on: appearance (e.g., based on appearance encoding distance or similarity, etc.), motion (e.g., actual vs predicted, etc.), a combination thereof, and/or other information. For example, the gametes can be matched based on appearance and motion features. This can increase the matching accuracy because gametes are asymmetric and rotate about a longitudinal axis during translation (e.g., successive images of the same gamete may look different). In a first example, the gametes can be matched based on appearance first, where predicted location is used as a tiebreaker. In a second example, the gametes can be matched based on location first (e.g., to identify candidate gametes or image segments), wherein appearance-based matching is localized to the predicted gamete location. In a third example, appearance and predicted location-based matching are performed independently, wherein a gamete is considered a match if both methods agree. However, the gametes can be otherwise tracked.

When the image is a sub-image (e.g., of a subregion of the scene), the method can additionally include combining the appearance encoding and/or predicted gamete locations across all sub-images, such that the gamete is tracked across the entire scene. Alternatively, the gamete can be tracked within sub-images only, wherein gametes that cross subregion boundaries are ignored.

However, a track for a gamete can be otherwise determined.

The method can optionally include determining a sub-video depicting the gamete S300, which can function to generate a set of sub-images, specific to the gamete, for downstream use (e.g., to provide to the specialist set, to determine attribute values, etc.). By limiting the visual input to the region surrounding the gamete (e.g., including only the gamete or including a limited set of adjacent gametes), S300 can decrease the model input noise, which, in turn, can result in more accurate model outputs. The sub-video is preferably for the gamete tracked in S200, but can alternatively be for any other gamete.

One or more sub-videos can be generated for each gamete. For example, multiple sequential, temporally-overlapping, and/or spatially-overlapping sub-videos can be generated for the same gamete. In this example, attribute values extracted from different sub-videos for the same gamete can be collectively used to determine the true attribute values for the gamete, or be otherwise used.

S300 can be performed in real-time with S100, asynchronously with S100, after S200 (e.g., immediately after, asynchronously, etc.), and/or at any other time. The sub-video is preferably determined based on the video sampled in S100, but can alternatively be independently sampled (e.g., sampled based on the track determined in S200). One or more sub-videos can be generated for one or more gametes (e.g., contemporaneously, concurrently, asynchronously, etc.). Sub-videos generated for the same or different gamete can be generated from the same or different videos.

The sub-video can be constructed such that the gamete is centered in the sub-video (e.g., wherein the sub-video field of view dynamically follows the gamete), constructed such that the gamete is always visible or depicted, but not necessarily centered in the sub-video, and/or otherwise constructed. Each sub-video can depict a single gamete (e.g., the tracked gamete; exclude other gametes; etc.), multiple gametes (e.g., the tracked gamete and adjacent gametes), and/or any other set of gametes.

The sub-video can include: a subset of each image (e.g., cropped images, image segments, sub-images, etc.), a subset of the image timeseries (e.g., spanning a limited time period, be a video clip, etc.), and/or otherwise defined relative to the video.

The sub-video frame size and/or field of view can be: predetermined (e.g., set for all gametes), dynamically determined (e.g., based on the gamete track, including: extent of travel, path length, etc.), and/or otherwise determined. The sub-video field of view can be static or dynamic (e.g., moving) relative to the scene, static or dynamic relative to the tracked gamete, and/or have any other relationship to the scene or gamete. The images included in the sub-video are preferably consecutively sampled, but can additionally or alternatively be contemporaneously sampled (e.g., sampling every other frame from the video), be frames satisfying a predetermined set of criteria (e.g., frames that depict the flat side of the gamete), and/or be any other set of images. In variants, the sub-video can be displayed at a higher resolution than the video. For example, if imaging data is sampled at 36 megapixels, but a display screen is only 4000 pixels, the full video must be downsampled for display, while the sub-video can be displayed at full resolution (e.g., depicting details of a gamete in the sub-video). However, the video and sub-video can be otherwise displayed.

The sub-video preferably spans a timeframe (e.g., duration) shorter than that of the video, but can alternatively span an equal or longer timeframe. The sub-video preferably spans an evaluation period (e.g., evaluation epoch), but can alternatively span any other timeframe. The evaluation period can be: manually determined, statistically determined (e.g., amount of time selected such that the probability of a predetermined event occurring exceeds a threshold), dynamically determined (e.g., based on gamete attribute values and/or confidence scores), and/or otherwise determined. In a first variant, the evaluation period is a predetermined length of time. For example, the predetermined length of time can be determined such that the sub-video has a high probability (e.g., above a threshold) of depicting an image of the gamete in a specific orientation (e.g., depicting the flat side of the gamete). Examples of evaluation period lengths include: 1 s, 2 s, 3 s, 4 s, 5 s, 6 s, 7 s, 8 s, 9 s, 10 s, 15 s, 20 s, 25 s, 30 s, and/or any other time. In a second variant, the evaluation period is dynamically determined. In a first example, the evaluation period is determined based on gamete tracking (e.g., S200), where the evaluation period is defined such that a threshold number of frames are captured with the gamete in the specific orientation. In a second example, the evaluation period is determined based on a gamete attribute model confidence score (e.g., where the sub-video extends until the confidence score plateaus, until the confidence score decreases past a threshold, etc.). In a third variant, the evaluation period is the length of the video. For example, the sub-video can be a timeseries of images (e.g., cropped images) across the entire length of the video. However, the evaluation period can be otherwise determined.

The relationship between different sub-videos for the same or different gametes can be: spatially and/or temporally overlapping or non-overlapping; spatially and/or temporally consecutive (e.g., adjacent) or non-consecutive; and/or otherwise configured.

Figure 16A:
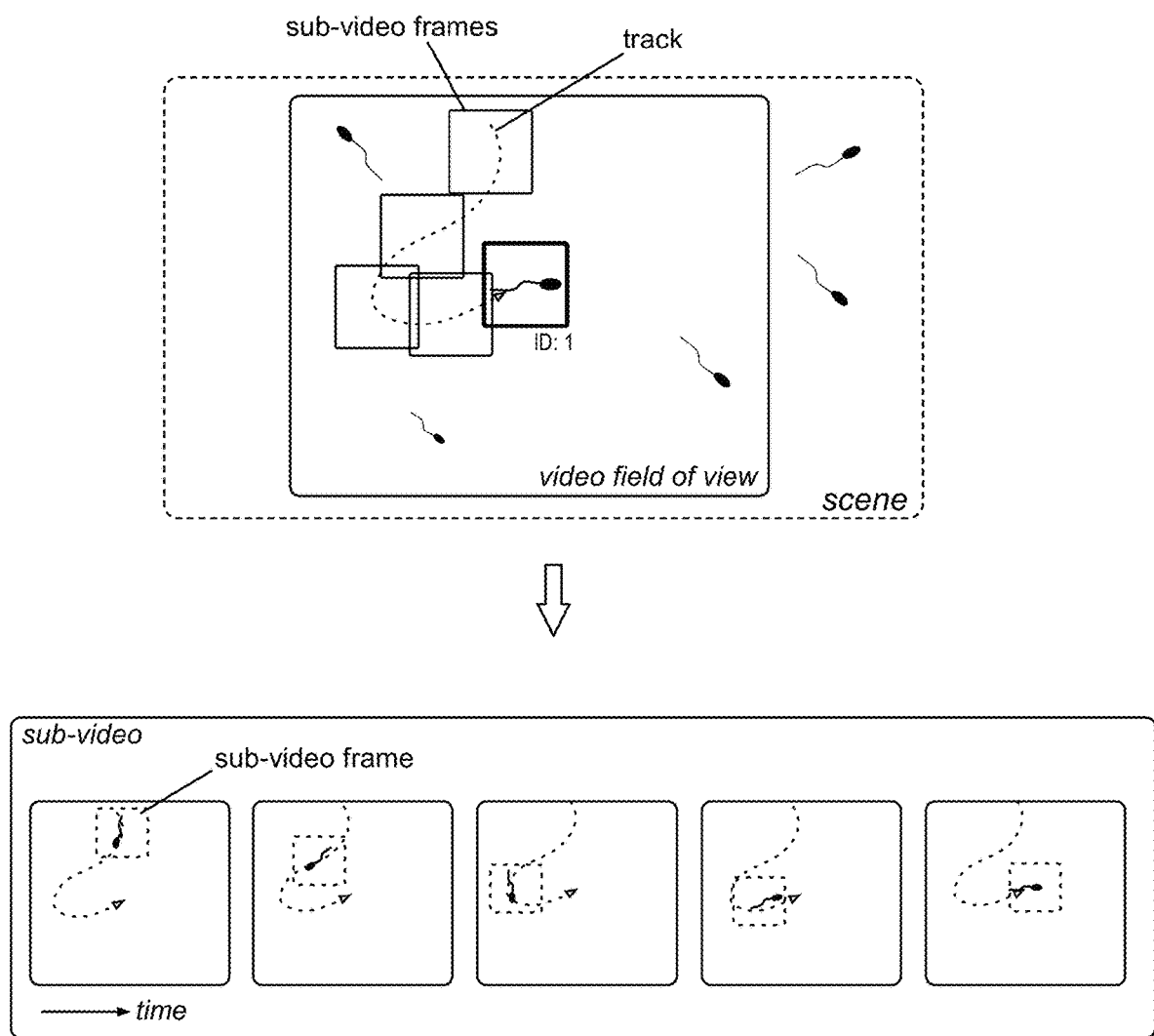
FIG. 16A depicts a first illustrative example of determining a sub-video of a gamete.
Figure 16B:
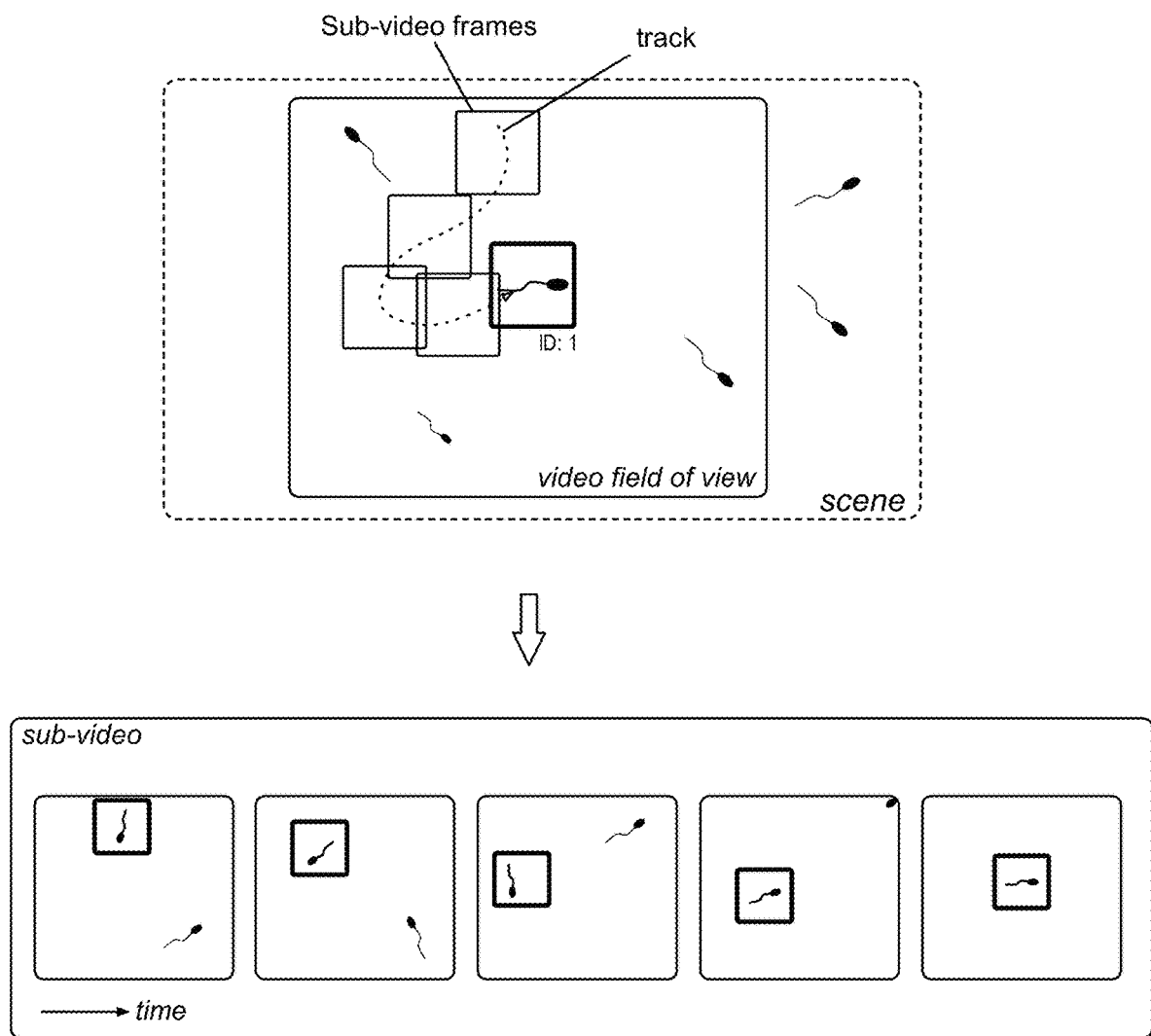
FIG. 16B depicts a second illustrative example of determining a sub-video of a gamete.

In a first variant of S300, the video images are segmented into gamete image segments after gamete identification. The image segments are then assigned a common gamete identifier after gamete matching and aggregated into a timeseries to generate the sub-video. In a second variant of S300, image segments of the gamete are extracted from each image based on the gamete position for each image timestep (e.g., based on S200). In a first embodiment of the second variant, the image segments cooperatively form frames of the sub-video (e.g., wherein the image segments can be positioned relative to the full frame coordinates; aligned with each other; etc.). In a second embodiment of the second variant, the image segments are overlayed in the respective gamete position over a blank image (e.g., black image, white image, uniform color image, reference background image, etc.) representative of a reference image and/or scene (e.g., full scene, partial scene, etc.), such that the resulting sub-video displays only the gamete moving through the full-frame image without displaying the other gametes (example shown in FIG. 16A). In a third variant of S300, a bounding box or other indicator that tracks the gamete through the frame can be rendered over the images of the sub-video (example shown in FIG. 16B). In this variant, the sub-video can include full frame images and/or cropped images (e.g., cropped to the maximum extent of gamete motion during the evaluation period, otherwise cropped).

The gamete sub-video and/or any other gamete information is preferably stored in association with a unique identifier for the gamete (gamete identifier); alternatively, the gamete information can function as the unique gamete identifier (e.g., wherein the gamete information is determined using the same method to identify the gamete).

However, the sub-video can be otherwise determined.

The method can optionally include generating a 3D model of the gamete. The 3D model can be used for determining attribute values (S400), such as geometric gamete attribute values (e.g., curvature, angle, dimensions, orientation etc.), and/or be otherwise used. In an illustrative example, the 3D model can be used to determine that a video image depicts the gamete rotated 30 degrees about its longitudinal axis such that the flat side of the gamete is partially obscured. The 3D model and/or other geometric representations can be generated based on the full video associated with the gamete, the sub-video associated with the gamete, one or more images associated with the gamete, the track for the gamete, and/or any other suitable information. The 3D model can be generated using structure from motion, using 3D reconstruction models, using stereovision or depth information (e.g., wherein the 3D model is regenerated using the resultant depth cloud and estimated gamete orientation), using other photogrammatic techniques, fitting a parameterized 3D model using the different viewpoints of the gamete, using reconstruction from depth or height information, and/or other methods. In a first variant, the 3D model can be generated from a 3D image of the gamete (e.g., acquired using the imaging system). In a second variant, the 3D model can be constructed from the multiple views (e.g., 2D views) presented while the gamete moves (e.g., swims). However, the 3D model of the gamete can be otherwise generated.

Determining attribute values for the gamete S400 can function to calculate, predict, and/or otherwise determine selection metrics used to evaluate gamete quality and/or compare gametes against each other. S400 can be performed after S200, after S300, after S700 (e.g., where S400 uses the trained model), after S500 (e.g., where S400 is performed for one or more selected gametes), during S100 (e.g., for a successive evaluation epoch), and/or at any other time. S400 can be performed at a predetermined frequency (e.g., each image, every N images, etc.); after a threshold condition is met (e.g., after a sub-video is generated, after a predetermined number of images have been captured, after a confidence score exceeds a threshold, etc.); once for each method instance (e.g., based on a keyframe); iteratively (e.g., until a stop condition is met); continuously; every evaluation epoch; and/or at any other suitable time. S400 can be performed once or multiple times for each gamete (e.g., based on the same or different sub-video). For example, S400 can generate a timeseries of attribute value sets for a given gamete based on a timeseries of sub-videos. S400 can be performed at a remote computing system, at a local computing system, and/or performed by any other system. S400 can be performed in real- or near-real time relative to sampling the video (S100).

Each gamete can be associated with a set of attribute values. The set of attribute values can include: different values for the same attribute (e.g., a timeseries of values for an attribute, etc.); values for different attributes (e.g., extracted from the same evaluation period, etc.); different values for different attributes (e.g., a timeseries of values for each of a set of attribute values); and/or any other suitable attribute values. The attribute values within the set can be: learned (e.g., using explainability methods, inferred from attribute value weights extracted from a model trained end-to-end to predict a probability of success based on other attributes, etc.), manually specified, and/or otherwise determined.

The gamete attribute values can be: predicted, calculated, or otherwise determined. Examples of attribute values include: a rating or score (e.g., quantitative, relative, qualitative, etc.), a ranking, a classification, a label (e.g., specialist label as described in S700), a degree of healthiness and/or normality (e.g., relative to a reference gamete population), a probability (e.g., probability of selection by a specialist, probability of successful post-fertilization development, etc.), morphology attribute value, motility attribute value, gamete measurement (e.g., destructive information values, DFI, PGT, vitality, etc.), post-fertilization development data, and/or values for any other attribute. Attribute values can be: qualitative, quantitative, relative, discrete, continuous, a classification, numeric, binary, and/or be otherwise characterized. Qualitative and/or relative characterizations can optionally be converted to quantitative characterizations (e.g., for aggregation S450, for selection S500, etc.). In variants, attribute values can be more similar to clinical selection methods, and therefore be more certifiable.

Figure 3:
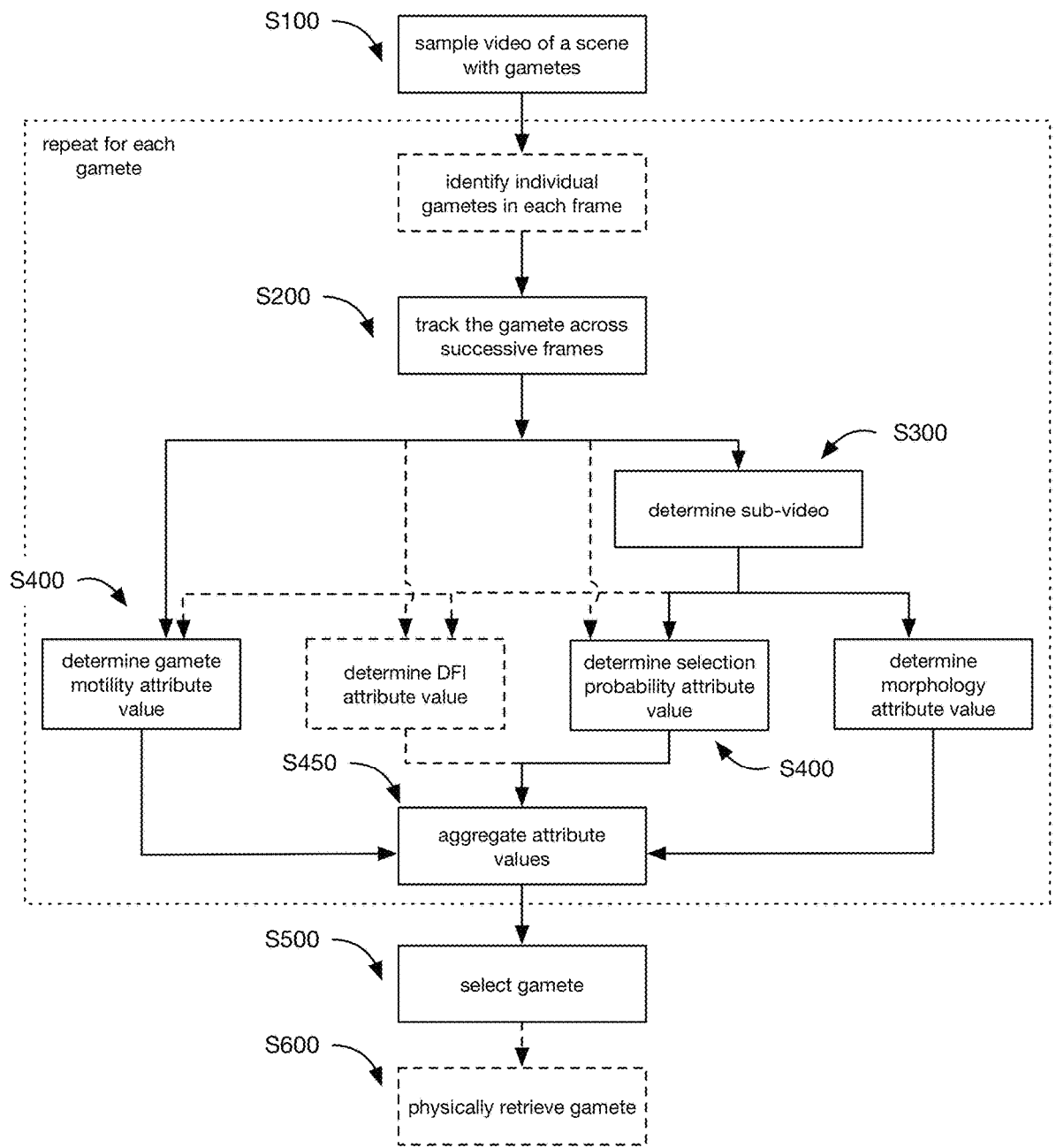
FIG. 3 is a schematic representation of an example of the method.
Figure 9:
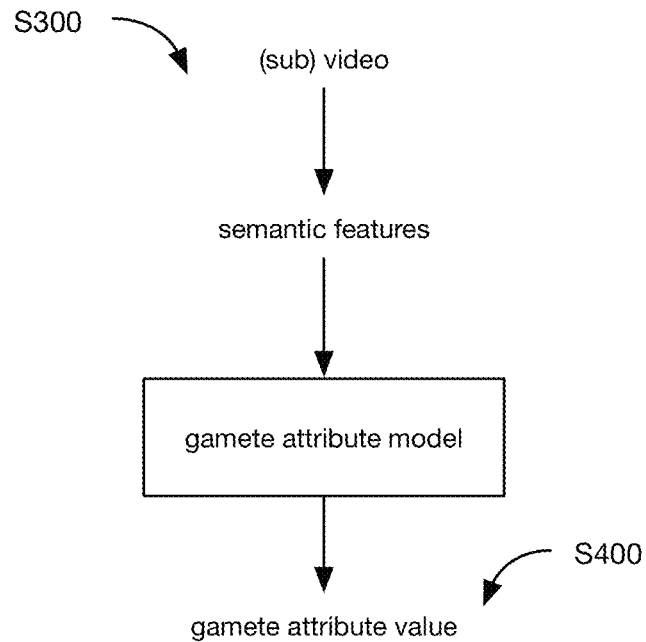
FIG. 9 depicts an example of using semantic features to determine an attribute value.
Figure 10:
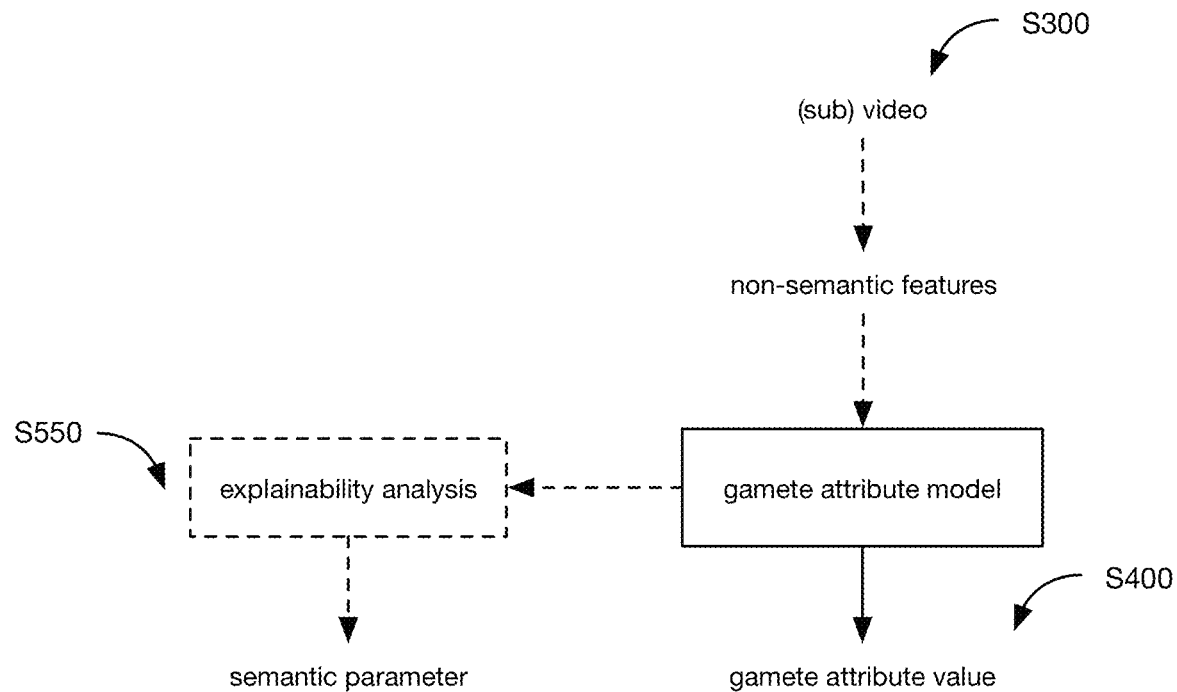
FIG. 10 depicts an example of using non-semantic features to determine an attribute value.

Gamete attribute values can be determined based on a set of inputs, including one or more of: the video, one or more sub-videos, gamete features (e.g., motility features and/or morphology features extracted from a video and/or sub-video); determined using traditional approaches; etc.), a gamete track (e.g., from S200), feature descriptors extracted from the video and/or sub-videos (e.g., nonsemantic and/or semantic features; examples shown in FIG. 9 and FIG. 10), attribute values for the gamete from prior evaluation periods, attribute values for other gametes (e.g., in the sample), a combination thereof, and/or any other suitable noninvasive or nondestructive inputs, and/or exclude any of the above (e.g., example shown in FIG. 3). In a specific example, inputs (e.g., to determine a selection probability attribute value and/or any other attribute value) can exclude semantic features extracted from the video, sub-video, and/or images (e.g., the selection probability can be predicted without using semantic features extracted from the sub-video). However, any other input can be used.

The inputs and/or the gamete attribute values are preferably stored in association with a unique identifier for the associated gamete, but can be otherwise stored.

The inputs can be filtered, weighted (e.g., where weights can be learned during model training S700; manually determined; etc.), selected, downsampled, upsampled, limited to a predetermined length or time window, limited to a predetermined number of datapoints (e.g., subsampled to obtain the correct frequency), and/or otherwise preprocessed. However, the inputs can alternatively be unprocessed.

Figure 14:
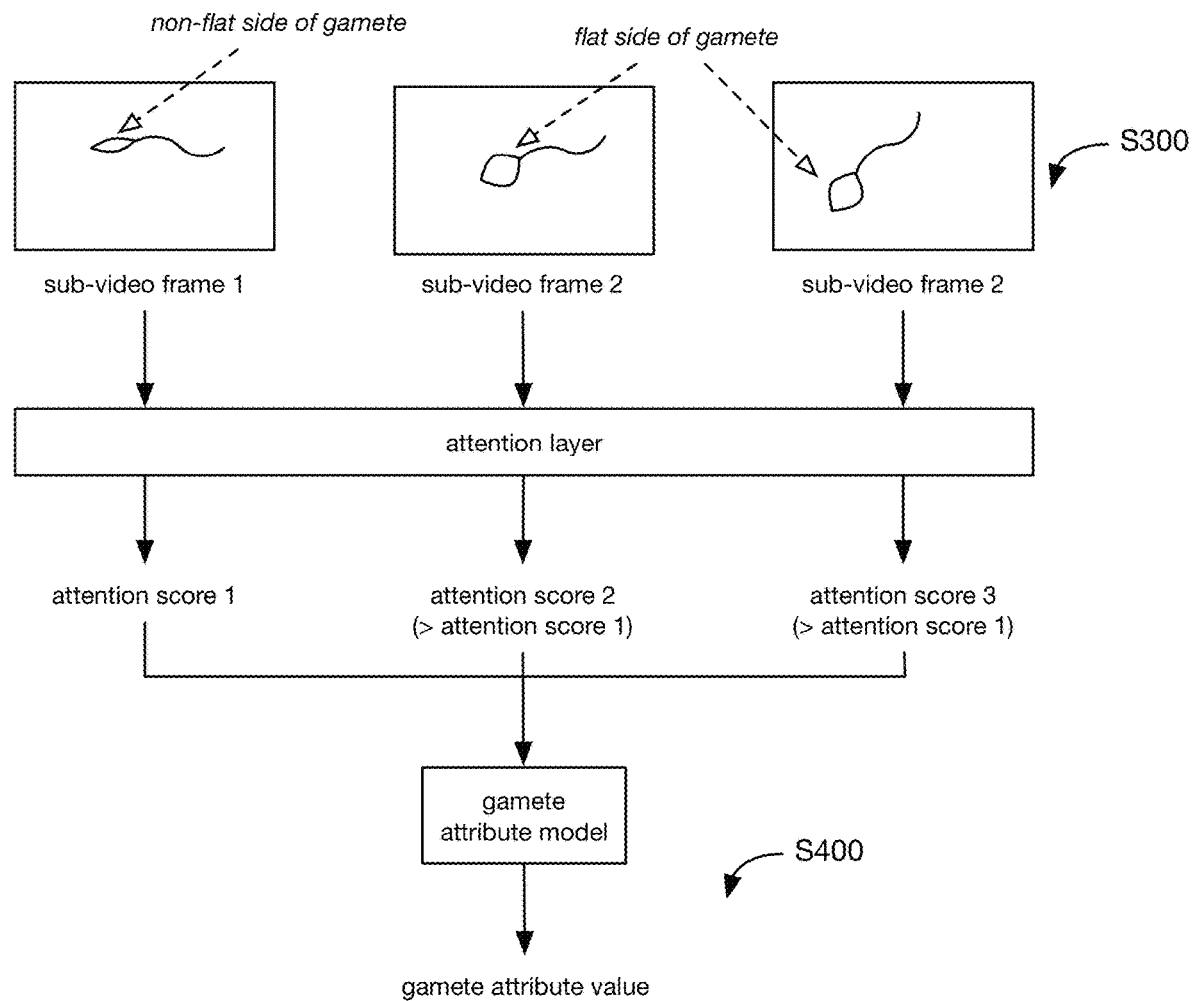
FIG. 14 depicts an illustrative example of an attention layer.

In one embodiment, image inputs can be weighted and/or selected based on the orientation of the gamete in the image relative to the imaging system and/or scene. In an illustrative example, a first frame depicting the gamete where the flat side of the gamete is 95% visible in the image can be weighted higher than a second frame depicting the gamete where the flat side is 20% visible in the image. In a first example, image selection and/or weighting can be performed using an attention model, wherein inputs (e.g., features extracted from each frame) are weighted based on an attention score (e.g., for the frame) determined using the attention model (e.g., example shown in FIG. 14). The attention score for a frame can be positively correlated with the frame depicting the flat side of the gamete (e.g., the flat side is parallel to the camera, parallel to the scene, etc.). The attention model can be part of the gamete attribute model (e.g., where the gamete attribute model uses attention layers, where the gamete attribute model includes an attention mechanism, etc.) or alternatively separate from the gamete attribute model (e.g., where the attention model pre-selects and/or pre-weights the images). In variants, the attention model, layers, and/or mechanism can be trained (e.g., explicitly or as part of an end-to-end model) to focus or upweight images depicting a flat side of the gamete, images depicting gametes, and/or any other subject. In a second example, the orientation of the gamete can be determined by calculating the surface area of the gamete visible in the image, where the image is selected when the surface area exceeds a threshold. In a third example, the orientation of the gamete can be determined by fitting a geometric shape (e.g., ellipse, polygon, etc.) to the gamete head, where the image is selected when the fit is above a threshold percentage. In a fourth example, the orientation of the gamete can be determined by using the 3D model of the gamete, where the image is selected when more than a threshold proportion of the flat face (e.g., identified on the 3D model) is depicted in the image. However, the gamete orientation can be otherwise determined, and/or the gamete images can be otherwise selected or weighted.

Figure 17A:
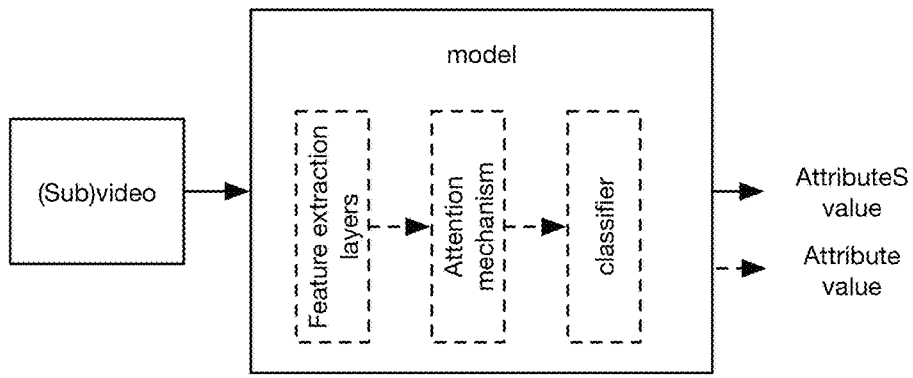
FIG. 17A depicts an example of a machine learning model.
Figure 17B:
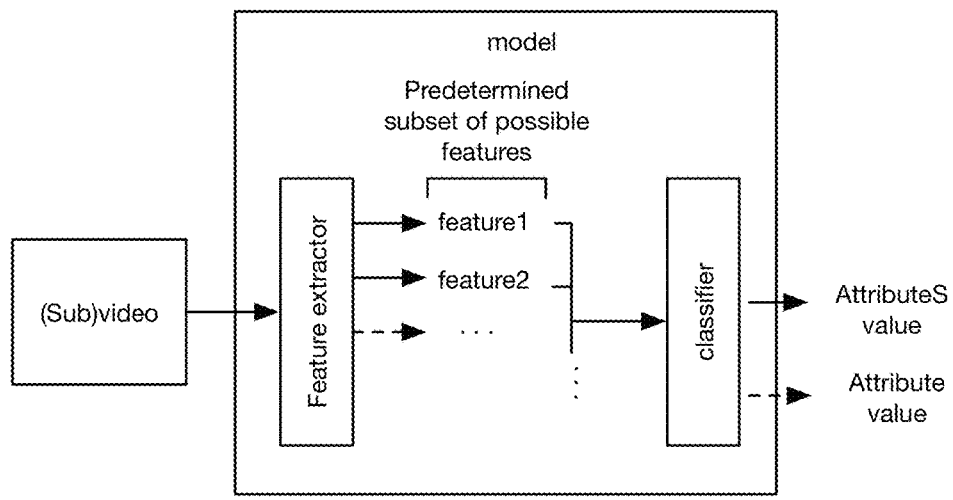
FIG. 17B depicts an example of a classical model

Gamete attribute values can be: manually determined (e.g., as described in S700), determined using a gamete attribute model, determined using explainability methods (e.g., as described in S550), determined experimentally (e.g., as described in S700), and/or otherwise determined. The gamete attribute model can be a classical model or traditional model (e.g., manually coded, with parameter values fixed using statistical calculations, extracting only a predetermined subset of possible features, etc.; example shown in FIG. 17A) and/or can be a deep learning model (e.g., trained using end-to-end learning, with learned parameter values, with learned feature weights, extracting all or a learned subset of possible features, etc.; example shown in FIG. 17B).

In a first variant, the gamete attribute values can be manually determined (e.g., as described in S700). Attribute values can be determined by a user (e.g., by the specialist set, as described in S700), verified and/or adjusted by a user, transmitted by a user (e.g., wherein a user inputs experimental results as attribute values), and/or otherwise determined.

In a second variant, the gamete attribute values can be experimentally determined (e.g., as described in S700).

In a third variant, the gamete attribute values can be determined using one or more gamete attribute models. In this variant, the attribute value (e.g., including attribute values for different gamete components) can be determined using a single model, be determined using multiple models (e.g., each trained to determine an attribute value for the respective attribute; an ensemble of models; etc.), and/or any set of models.

Figure 5:
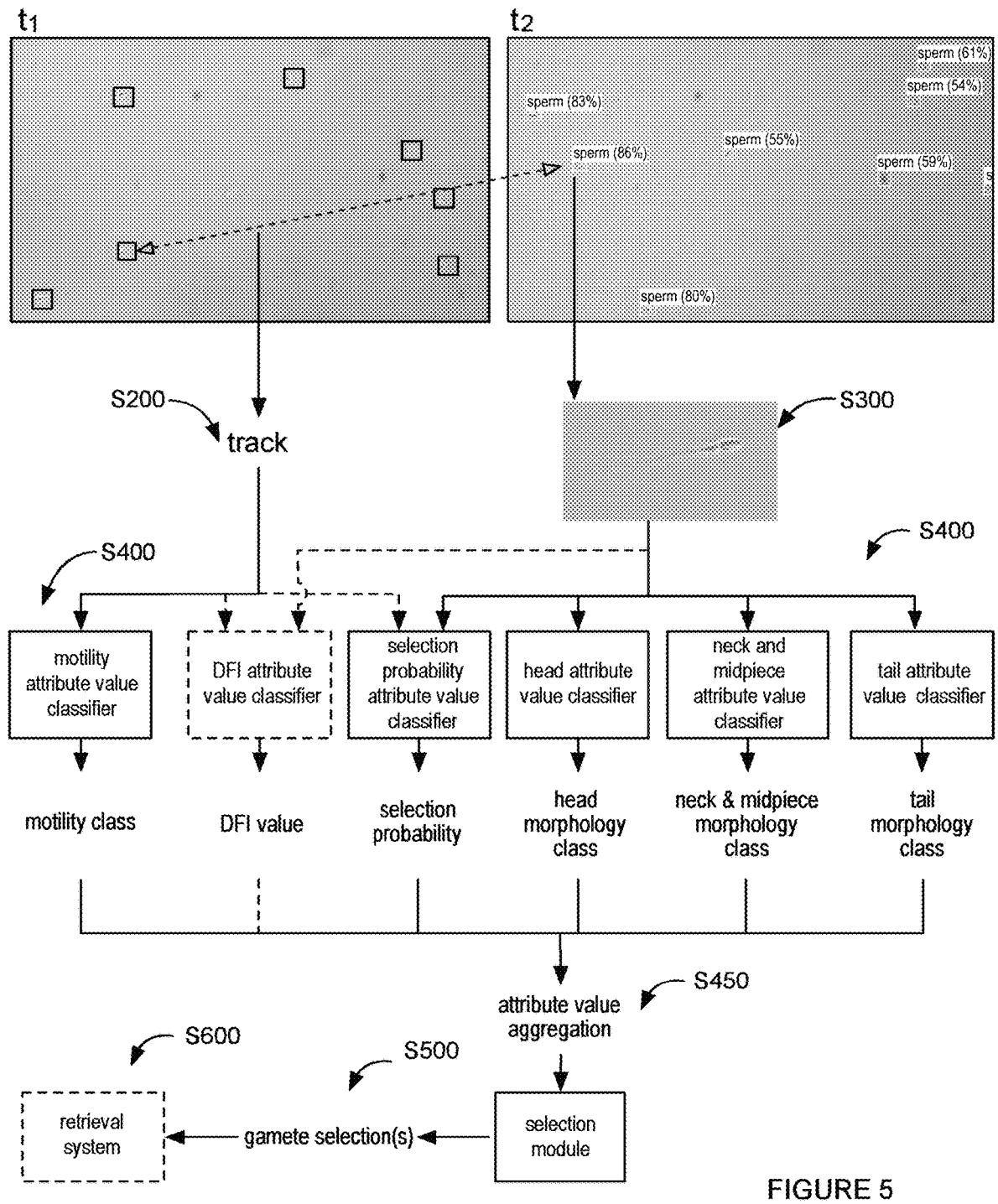
FIG. 5 depicts an example of determining a set of attribute values.

In a first embodiment, the system includes a set of gamete attribute models, each configured to output a gamete attribute value for a different gamete attribute or class thereof (e.g., overall or gamete component-specific: morphology, motility, selection probability, etc.). These gamete attribute models can be traditional models, deep learning models, and/or a combination thereof. In a first example, a morphology, motility, and selection probability model are used to determine a morphology attribute, a motility attribute, and a selection probability attribute, respectively. In a second example, different models are used for each morphology component attribute (e.g., head defects, neck and midpiece defects, principal piece defects, etc.). An example is shown in FIG. 5.

In a second embodiment, the system includes a single model (e.g., a multiclass classifier), configured to output values for one or more gamete attributes. This model is preferably a deep learning model (e.g., a trained machine learning model), but can alternatively be a traditional model. For example, a single model predicts a selection probability, motility attribute values, morphology attribute values, a probability of successful fertilization, a DFI value, and/or any other value.

Figure 17C:
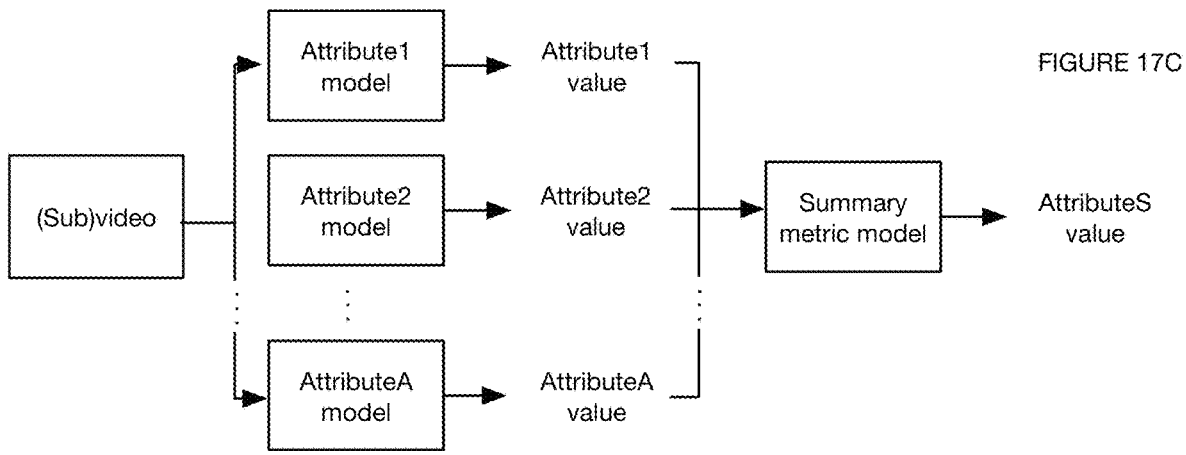
FIG. 17C depicts an example of a model ensemble.

In a third embodiment, the gamete attribute model is an ensemble of sub-models, wherein upstream sub-models output a subset of gamete attributes, and downstream sub-models determine additional gamete attribute values based on the values output by one or more of the upstream models, example shown in FIG. 17C. The upstream sub-models can be traditional models and the downstream sub-models can be deep learning models; alternatively, the upstream and downstream sub-models can be traditional models, deep learning models, and/or a combination thereof. For example, upstream models can include motility, morphology, and DFI models that predict motility, morphology and DFI attribute values based on a (sub)video depicting a gamete, wherein a downstream model can predict the selection probability based on the motility, morphology, and DFI attribute values.

For example, a motility model, a morphology model, and a DFI model each output attribute values (e.g., semantic features) based on the input (e.g., a sub-video for the gamete). These outputs are then ingested by a secondary gamete attribute model to determine an overall selection metric (e.g., classifying the gamete into a select or do not select class).

However, the gamete attribute model can be otherwise constructed.

The gamete attribute model(s) can be: classical or traditional models, deep learning models, leverage a combination thereof, and/or any other suitable mode.

In a first embodiment, the gamete attribute models are classical or traditional models, wherein the features can be manually selected, the parameters can be manually encoded, the feature transforms can be manually defined, and/or any other suitable portion of the model can be manually specified. For example, the attribute values can be determined using an equation, lookup table, scoring engine, kinematic model, dynamic model, geometric model, computer-aided sperm analysis (CASA) methods, computer-aided sperm morphometric assessment (CASMA) methods, and/or any other method. In this embodiment, the attribute values are preferably determined based on semantic features (e.g., geometric measurements, motion measurements, etc.) extracted from one or more images, but can alternatively be determined based on non-semantic features.

A first example of classical model use includes extracting motion attribute values for the gamete. The motion attributes can include: gamete kinematics (e.g., velocity, acceleration, etc.), heading, summary features (e.g., average path or velocity, curvilinear path or velocity, straight-line path or velocity, amplitude of lateral head displacement, linearity, wobble, straightness, beat-cross frequency, mean angular displacement, etc.), and/or other features. The kinematics can be linear, rotational, and/or motion in other degrees of freedom. Illustrative examples of calculated motility attribute values include: curvilinear velocity (e.g., time-averaged velocity of a gamete head along its curvilinear path), straight-line velocity (e.g., time-averaged velocity of a gamete head along the straight line between a first and second detected positions), average path velocity (e.g., time-averaged velocity of a gamete head along its average path), amplitude of lateral head displacement (e.g., magnitude of lateral displacement of a gamete head), linearity, wobble (e.g., measure of oscillation of the actual path about the average path), beat-cross frequency (e.g., the average rate at which the curvilinear path crosses the average path), mean angular displacement (e.g., the time-averaged absolute values of the instantaneous turning angle of the sperm head along its curvilinear trajectory), similarity to a helix, CASA variables, and/or any other calculated mobility parameter. This is preferably performed using temporally adjacent images (e.g., images from two or more timesteps), but can alternatively be performed using a single image and motion features from a prior timestep or using other input. The motion features can be extracted using: a physics model, motion model, motion estimators, optical flow (e.g., for higher gamete concentrations or scenes with more visual features), filtering and data association (e.g., Kalman filter, particle filter), target representation and localization (e.g., kernel-based tracking, contour tracking), a trained DNN, calculated using an equation, and/or other motion modules.

A second example of classical model use includes determining the current gamete location and/or orientation (e.g., pose) within the scene. The gamete location (e.g., position) and/or orientation is preferably specified relative to a global (scene) coordinate system or reference image, but can alternatively be relative to another reference image. In a first embodiment, the gamete location and/or orientation is preferably determined based on the pixel indices of the gamete's pixels within the image and the scene coordinates associated with said pixel indices, but can be otherwise determined. In a second embodiment, the gamete location and/or orientation is determined based on a distance to a known scene reference. However, any object localization and/or orientation method or module can be used.

A third example of classical model use includes estimating a predicted location for the gamete. The predicted location is preferably the predicted gamete location within the next image (e.g., for timestep t+1), but can alternatively be the gamete location (e.g., within the image or within the scene) N images into the future and/or the past. This example can be performed using the current location, the gamete's motion features, the entire image, an image segment, and/or other input. The predicted gamete location can be estimated using a motion model, a filter (e.g., Kalman filter, Particle filter), be calculated, be looked up, and/or be otherwise determined.

A fourth example of classical model use includes determining a gamete morphology attribute value based on a predetermined set of gamete appearance features (e.g., geometric dimensions, appearance encoding, etc.) extracted from one or more images. The gamete appearance features can include: gradients, edges, corners, blobs, boundaries, and/or any other visual feature. The gamete appearance features are preferably nonsemantic, but can alternatively be semantic. The appearance features can be extracted using: segmentation methods (e.g., instance-based segmentation, semantic segmentation, etc.), object detection methods (e.g., Viola-Jones, SIFT, HOG, region proposals, SSD, YOLO, etc.), image segmentation methods (e.g., motion based segmentation, thresholding, etc.), masking methods, and/or other methods. In this example, features used to calculate the gamete morphology value can be manually selected (e.g., the head boundary is used to determine the head shape score or classification), or otherwise selected. In this example, the morphology attribute value can be: classified, calculated, and/or otherwise determined based on the appearance feature values. Illustrative examples of calculated morphology attribute values include: head and mid-piece dimensions (e.g., length of major and minor axes), head ellipticity and regularity, neck angle, tail length, width, curvature (e.g., coiling), vacuole parameters (e.g., number, density, area per vacuole, overall area, vacuole ratio relative to head), stain-dependent measurement of the acrosome area, CASMA variables, and/or any other calculated morphology parameter.

In a second embodiment, gamete attribute models are machine learning (ML) models, wherein feature selection, weighting, relationships, and/or other model aspects can be automatically learned. The machine learning model is preferably the gamete attribute model (e.g., trained in S700) to output a set of gamete attribute values (e.g., a predicted gamete attribute value) based on the inputs. However, the model can be otherwise trained. The ML models can predict, infer, or otherwise determine the respective gamete attribute value(s). The ML models can ingest the video, one or more sub-videos, auxiliary data (e.g., population-level data, attribute values for the gamete from a prior evaluation period, etc.), and/or any other information.

In a first example of ML model usage, a gamete motility attribute value is determined using a gamete attribute model, wherein the gamete attribute model includes one or more trained neural networks (e.g., trained in S700 based on specialist-labeled images or tracks). The trained models (such as neural networks) can include motility classifiers (e.g., a multiclass classifier), a cascade of classifiers, regression models (e.g., calculating a motility attribute value for a given motility ontological class), and/or any other suitable model.

In a second example of ML model usage, a gamete morphology attribute value is determined using a gamete attribute model, wherein the gamete attribute model includes one or more trained models (such as neural networks) (e.g., trained based on specialist-labeled images in S700). The trained models can include morphology classifiers (e.g., multiclass classifiers), a cascade of classifiers, regression models (e.g., calculating a morphology attribute value for a given morphology ontological class), and/or any other suitable model.

In a third example of ML model usage, a DFI attribute value is determined using a trained gamete attribute model, which can function to predict DFI values without destroying the gamete or rendering the gamete unviable. In this example, the gamete attribute model is preferably trained (in S700) based on images and/or videos of gametes associated with measured DFI values, but can be otherwise trained. The DFI attribute value is preferably a score, but can alternatively be a class (e.g., representing one or more DFI value ranges), and/or any other suitable DFI characterization.

However, attribute values can be determined using a combination of the above or otherwise determined.

The method can optionally include determining a confidence score for a gamete attribute value S470, which can function to determine an uncertainty parameter which can be used in gamete selection (S500), model training (S700), and/or other downstream processes. S470 can be performed after S450, after S400, prior to S500 (e.g., where a gamete is selected based on a high or low confidence score), and/or at any other time. In a first variant, the confidence score can be based on a statistical measure of the distribution of attribute values for the gamete (e.g., standard deviation, variance, interquartile range, etc.). In a second variant, the confidence score can be determined by gamete attribute model (e.g., be the confidence score associated with the predicted value, etc.). In a third variant, the confidence score can be based on a determined gamete focus level (e.g., gamete image blur). However, the confidence score can be otherwise determined.

The method can optionally include aggregating gamete attribute values S450, which can function to determine a distribution of gamete attribute values for a given gamete attribute, to determine another gamete attribute value (e.g., a holistic selection metric, a combined attribute value, etc.) based on a combination of individual gamete attribute values, determine population-level attribute values, and/or to otherwise process gamete attribute values to improve gamete selection. The gamete attribute values can be for an individual gamete and/or for a set of gametes (e.g., a population). The gamete attribute values can be aggregated: manually, using a manually-determined model, using a trained machine learning model, and/or be otherwise aggregated.

Figure 4A:
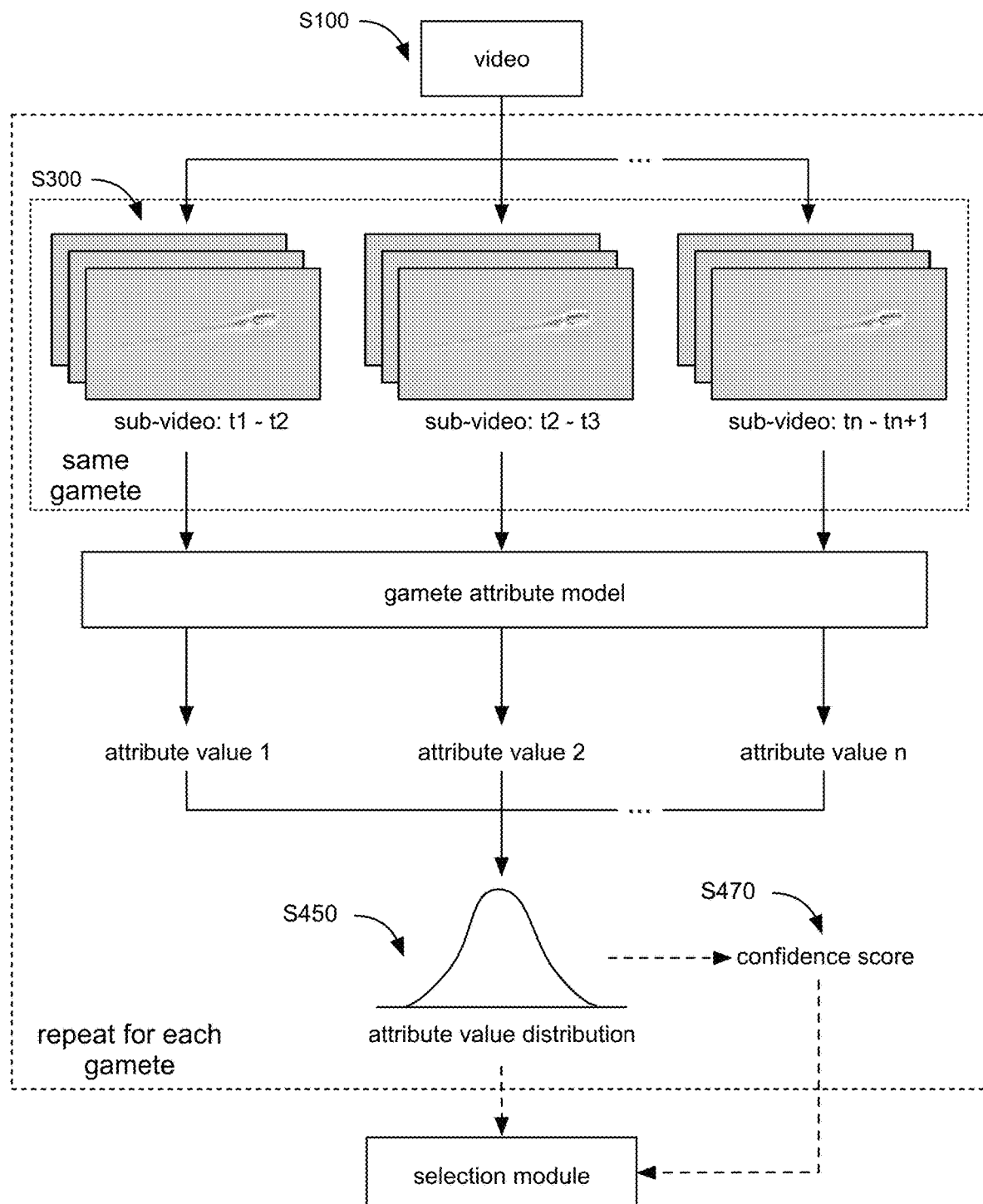
FIG. 4A depicts an example of aggregating attribute values.
Figure 4B:
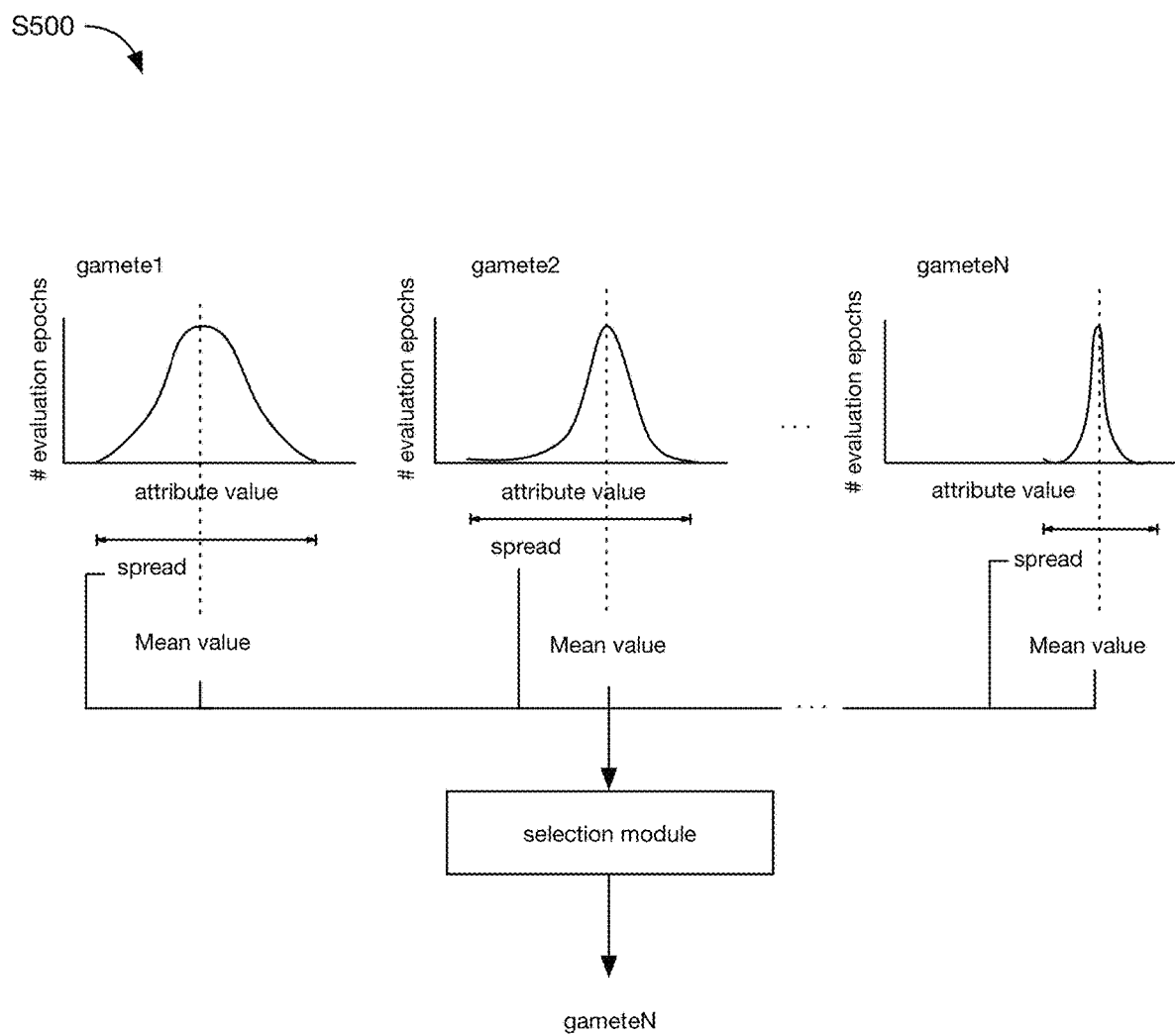
FIG. 4B depicts an example of selecting a gamete based on aggregated attribute values.

In a first variant, values for a gamete attribute are aggregated for a gamete into a final gamete attribute value. The attribute values can be aggregated across images (e.g., wherein the images can be selected and/or weighted as described in S400), across sub-videos and/or evaluation periods (e.g., where a gamete attribute value is determined for each sub-video), and/or across any other parameter. In a first embodiment, the values for the gamete attribute are averaged (e.g., weighted based on the respective confidence score from S470; weighted based on how much of the gamete's flat face is visible; etc.). In a second embodiment, the values for the gamete attribute are treated as votes, wherein the attribute value with the highest number, the majority, the supermajority, and/or any other vote proportion is used as the final attribute value. In a third embodiment, the attribute values are aggregated into a distribution (e.g., example shown in FIG. 4A), wherein the final gamete attribute value can be the mean or mode of the distribution. The spread, variance, standard deviation, interquartile range, and/or other statistical measure of the distribution can additionally or alternatively be determined (e.g., example shown in FIG. 4B).

In a second variant, the values for different gamete attributes from the same gamete can be aggregated into a summary metric for the gamete. The values that are aggregated can be from the same evaluation period or from different evaluation periods. The values that are aggregated can be: values directly extracted from the video and/or sub-video, values calculated using the first variant, and/or any other value. In a first embodiment, a score (e.g., the summary metric) can be calculated from values for different gamete attributes for the same gamete. For example, the values for different gamete attributes can be aggregated using a weighted sum (e.g., where different gamete attributes are associated with different weights). In an illustrative example, a holistic selection metric can be calculated as: 0.5*(motility attribute value)+0.4*(head morphology attribute value)+0.1*(tail morphology attribute value). The weights can be: manually assigned, learned (e.g., from specialist preferences), and/or otherwise determined. In a second embodiment, the score can be inferred by a trained machine learning model, based on one or more values for one or more gamete attributes. For example, a selection probability can be predicted for the gamete based on: one or more morphology attribute values, one or more motility attribute values, one or more DFI attribute values, one or more gamete population values (e.g., average morphology or motility; which standard deviation of the population the gamete is in; etc.), and/or any other suitable gamete attribute value or combination thereof.

In a third variant, S450 includes aggregating values across different gametes. This can function to provide population-level measures (e.g., population attributes), which can be used to: evaluate the sample, as an input into the selection process (e.g., used to rank or otherwise rate each gamete relative to the remainder of the sample), and/or otherwise used. The values are preferably for the same gamete attribute, but can alternatively be for different gamete attributes. The aggregated values can be: all values within the respective timeseries for each gamete; a final attribute value for each gamete (e.g., as determined using the first variant); and/or any other value. Examples of population-level measures can include population-level values for: motility attributes (e.g., velocity, amplitude of lateral head displacement, progressive motility, etc.), morphology attributes (e.g., head ellipticity and regularity, neck angle, tail length, etc.), DFI attributes, vitality attributes, and/or any other measure. The values can be: calculated from the aggregated values, a statistical measure of the aggregated values (e.g., mean, median, mode, variance, IQR, etc.), inferred or predicted from the aggregated values, and/or otherwise determined. However, values can be otherwise aggregated across different gametes.

However, attribute values can be otherwise aggregated.

Selecting the gamete S500 can function to select a gamete from a gamete population (e.g., sample). S500 can identify gametes for: isolation, retrieval (e.g., physically select the most viable gamete(s) retrieved for assistive reproductive processes), model training, additional attribute value determination by a gamete attribute model, training data generation (e.g., an instance of S500 is used to prefilter the gametes in the training population), and/or any other gamete use.

In a first example, high-quality gametes are selected for physical retrieval for IVF-ICSI. In a second example, high-quality gametes are selected, wherein the associated data (e.g., sub-video, gamete attribute values, etc.) are included in a training dataset (e.g., such that the training dataset has a higher proportion of viable gametes than would be the case for a reference gamete population, such as the sample). The training dataset can be used for: attribute model training, selection model training, and/or other model training. In a third example, gametes with high model uncertainty can be selected for manual labelling. In a fourth example, the gametes can be selected (e.g., using a first attribute value) to filter (e.g., pre-filter) gametes into a subset, wherein the gametes in the subset can then undergo additional attribute value determination (e.g., S400, S700, etc.) and/or selection (e.g., repeated S500). For example, a DFI value can be determined for each gamete based on the respective (sub) video, wherein gametes having a DFI value less than a threshold are selected (e.g., prefiltered). Values for selection attributes can then be extracted from the (sub)videos for the selected gametes, wherein the final gametes are selected based on the selection attribute values. The final gametes can optionally be post-filtered based on their values for postfiltering attributes (e.g., calculated by the model calculating the selection attributes or by another model executing in parallel). However, the gametes can be otherwise selected for other use cases.

S500 can be performed at a remote computing system, remotely by a user (e.g., the specialist set), at a local computing system, by a user local to the imaging system, and/or can be otherwise performed. One or more gametes can be selected. The selected gamete(s) is preferably assigned a unique gamete identifier (e.g., automatically, manually, etc.), but can be otherwise identified.

S500 can be performed after S400, after S470, after S470, during S700 (e.g., where attribute values are determined for selected gametes) and/or at any other time. S500 can be performed periodically, iteratively (e.g., for each of a set of evaluation periods), after a threshold condition is met (e.g., after a threshold number of gametes in a sample have been assigned attribute values, after a predetermined number of images have been captured, after a confidence level for a gamete attribute value exceeds a threshold, etc.); once for each method instance (e.g., based on a keyframe); iteratively, until a stop condition is met; and/or at any other suitable time. S500 can be performed in real- or near-real time for one or more gametes (e.g., while the gamete is being tracked in situ in the sample or scene), or be performed asynchronously.

The gamete (e.g., a target gamete) can be selected automatically (e.g., based on the respective gamete attribute values, aggregated gamete attribute values, confidence scores, etc.), manually (e.g., wherein predicted attribute values are presented to a user for user selection; wherein the gamete is selected by a specialist in S700; etc.), randomly, and/or be otherwise selected. The gamete can be selected using: a set of selection criteria, an equation (e.g., where gamete attribute values are variables in the equation), one or more selection models (e.g., a trained neural network), a ruleset or criteria, heuristics, decision trees, ranking algorithms, filters, and/or any other selection module. Any selection module can be: specified by a specialist, learned from historic specialist gamete selections, and/or be otherwise determined. In variants, the selection can be based on multiple gamete attribute values. Using multiple attribute values can more accurately replicate the specialist manual selection (e.g., by incorporating a more holistic evaluation of the gamete), can more accurately pick the optimal gamete for embryonic development, can decrease the computational load (e.g., by filtering gamete candidates using a first selection prior to applying a more computationally intensive gamete attribute model for a final selection), and/or otherwise improve the gamete selection process.

The gametes can be selected using a set of selection criteria, or be otherwise selected. Examples of selection criteria can include: gamete ranking within the population (e.g., select the top N % of the gamete sample, such as the top 1%, 2%, 5%, 10%, a range therein, etc.); whether the gamete satisfies one or more thresholds (e.g., attribute value thresholds, aggregate attribute value thresholds, predetermined thresholds, population-defined thresholds, etc.); whether the gamete attribute values have a predetermined pattern, whether the gamete attribute value is within a predetermined set of included and/or excluded attribute classifications (e.g., head must be classified as "normal"; head must not be classified as "amorphous", neck must not be "sharply bent," etc.); gamete comparison against one or more reference gametes (e.g., other gametes in the sample); and/or any other selection criteria or combination thereof.

In a first variant, a predetermined number or percent of gametes in the set can be selected. For example, the top 1% of gametes, ranked by quality, can be selected. High quality gametes can have: a high selection probability; a high fertilization success probability; a high pregnancy success probability; a high birth probability; a high summary metric; a low miscarriage probability; a predetermined set of attribute values (e.g., "normal" head, "normal" tail, etc.); and/or be otherwise defined. High values (e.g., probabilities, scores, etc.) can be: higher than the remainder of the population, higher than a proportion of the population, higher than a predetermined value, and/or otherwise defined. Alternatively, the bottom N % of gametes (e.g., ranked by quality) can be selected, and/or any other suitable proportion of gametes can be selected.

In a second variant, gametes are selected based on one or more statistical measures of distributions for one or more gamete attributes aggregated over time (e.g., from S450). The statistical measure can be measure of location (e.g., central tendency, mean, mode, interquartile mean, etc.), measure of statistical dispersion or spread (e.g., absolute deviation, standard deviation, variance, range, interquartile range, distance standard deviation, etc.), measure of distribution shape (e.g., skewness, kurtosis), measure of statistical dependence (e.g., correlation coefficient), and/or be otherwise defined. In a first example, gametes associated with attribute value standard deviations greater than a threshold are excluded. In a second example, gametes associated with attribute value standard deviations smaller than a threshold are selected. In a specific example, a gamete with a highest statistical location and smallest statistical spread of the respective distribution is selected. In this embodiment, the threshold can be predetermined, defined by the gamete with the next-smallest standard deviation in the set of gametes, and/or be otherwise defined. In a third example, gametes with attribute values in the highest standard deviation or IQR are selected.

In this variant, the gamete attribute is preferably a single attribute, but can alternatively be multiple attributes. In a first example, the gamete is selected based on the statistical measure(s) of the gamete's timeseries of selection probabilities or pregnancy success. In a second example, the gamete is selected based on the statistical measure(s) of the gamete's morphology, motility, and/or DFI attributes. In an illustrative example, the selected gamete has attribute locations (e.g., average attribute values) exceeding a threshold for each attribute and has the lowest spread (e.g., relative to the population) for each of a predetermined set of attributes (e.g., all attributes, specialist-specified critical attributes, etc.). However, the gamete can be otherwise selected based on a statistical measure of a distribution.

In a third variant, gametes associated with an attribute value confidence score (S470) less than a threshold are selected (e.g., for additional model feedback S700).

In a fourth variant, a target gamete is selected when the gamete has satisfied a condition (a threshold condition, a comparison condition, etc.) for a threshold period of time and/or number of evaluation periods. In a first example, aggregated attribute values (e.g., statistical distribution spread, mean attribute values, etc.) satisfies the predetermined condition. In a second example, a target gamete is selected when its attribute value remains the highest ranked in comparison to other gametes in the field of view for a threshold period of time.

In a fifth variant, the gamete (e.g., target gamete) is selected when it satisfies the selection criteria better than a previously selected gamete (e.g., the reference gamete). For example, the target gamete is selected when its gamete attribute value is greater than the respective attribute value for the previously selected gamete. In another example, the target gamete is selected when the attribute values are more consistent over time (e.g., the statistical spread is lower) than the reference gamete. However, any other suitable set of selection or evaluation criteria can be used. The attribute values from the compared gametes can be drawn from: the same evaluation period(s), different evaluation periods, and/ or any other evaluation period. For example, the attribute values for the previously-selected gamete can be drawn from previous evaluation periods, while the attribute values for the target gamete can be drawn from the most current evaluation period(s).

In a sixth variant, the gamete can be selected when the values for a set of key gamete attributes satisfy a predetermined set of conditions. The key gamete attributes can be: manually specified, learned (e.g., using SHAP values, feature correlation methods, feature selection methods, etc.), and/or otherwise determined. Examples of conditions can include: the attribute value must be above or below a threshold value; the attribute value must be within a set of inclusionary values (e.g., "normal", etc.); the attribute value must not be within a set of exclusionary values (e.g., "abnormal", etc.); and/or other conditions.

In a seventh variant, the gamete can be selected based on a decision tree. For example, gametes with "normal" gamete components can be preferentially selected; gametes with "normal" values for highly-weighted attributes (e.g., specialist weighted attributes) can be selected if no gametes with all "normal" components are identified; and gametes with the highest values for a predetermined set of attributes (e.g., specialist-weighted attributes, automatically selected influential attributes, all attributes, etc.) are selected if no gametes with "normal" values for highly-weighted attributes are identified. However, any other decision tree can be used.

In an eighth variant, the gamete can be selected when it satisfies a condition (e.g., a comparison condition, a threshold condition, etc.) relative to one or more reference gametes. The reference gametes can be the gametes in the sample from which the selected gametes are derived, a normal (e.g., average) population of gametes, a normal population of gametes for a given demographic (e.g., the same demographic as the selected gametes), and/or any other reference. In a first example, the gamete is selected when its gamete attribute value is within the bounds of the reference gamete attribute values. In a second example, the gamete is selected from a set to generate a skewed gamete subset with a skewed distribution of gamete attribute values relative to a reference gamete population. In this example, S500 can select a set of gametes (e.g., filtered gametes, pre-filtered gametes, a gamete subset, etc.) for use in model training, such that the training data has a higher proportion of viable gametes than a reference population (e.g., the sample of gametes, a normal baseline population, etc.). Viable gametes can be defined as: gametes with a probability of selection greater than 20%, 30%, 40%, 50%, 60%, 70%, 80%, 90%; gametes with an attribute value greater than a threshold, motile gametes, and/or any other viability criteria. Normal gamete populations can have a low proportion of viable gametes; thus, this selection variant can enable a more balanced training data set and/or result in a more accurate prediction/selection of viable gametes.

In a ninth variant, a gamete is selected using a combination of selection criteria in a multi-stage selection. For example, gamete candidates can be selected (e.g., filtered, pre-filtered, etc.) from a gamete population based on a first (preliminary) attribute value determined for each gamete in the population in a first iteration of S400 (using a first model); the filtered gametes can then undergo a second selection based on a second attribute value determined for each gamete in the filtered set in a second iteration of S400 (using a second model). This multi-stage selection process can be continued for any number of attribute values and/or other selection criteria. In examples, the first attribute value can be a DFI attribute value and the second attribute value can be a selection probability; the first attribute value can be a selection probability and the second attribute value can be a DFI attribute value; the first attribute value can be a motility and/or morphology attribute features (e.g., directly extracted from a video and/or sub-video), the second attribute value can be a selection probability, and the third attribute value can be a DFI attribute value; however, any other combination of gamete attributes in any other order can be used. In variants, this multi-stage attribute value determination can reduce computational load by using a first model that is less computationally intensive than the second model (e.g., the first model is a classical model and the second model is a trained machine learning model).

Figure 11:
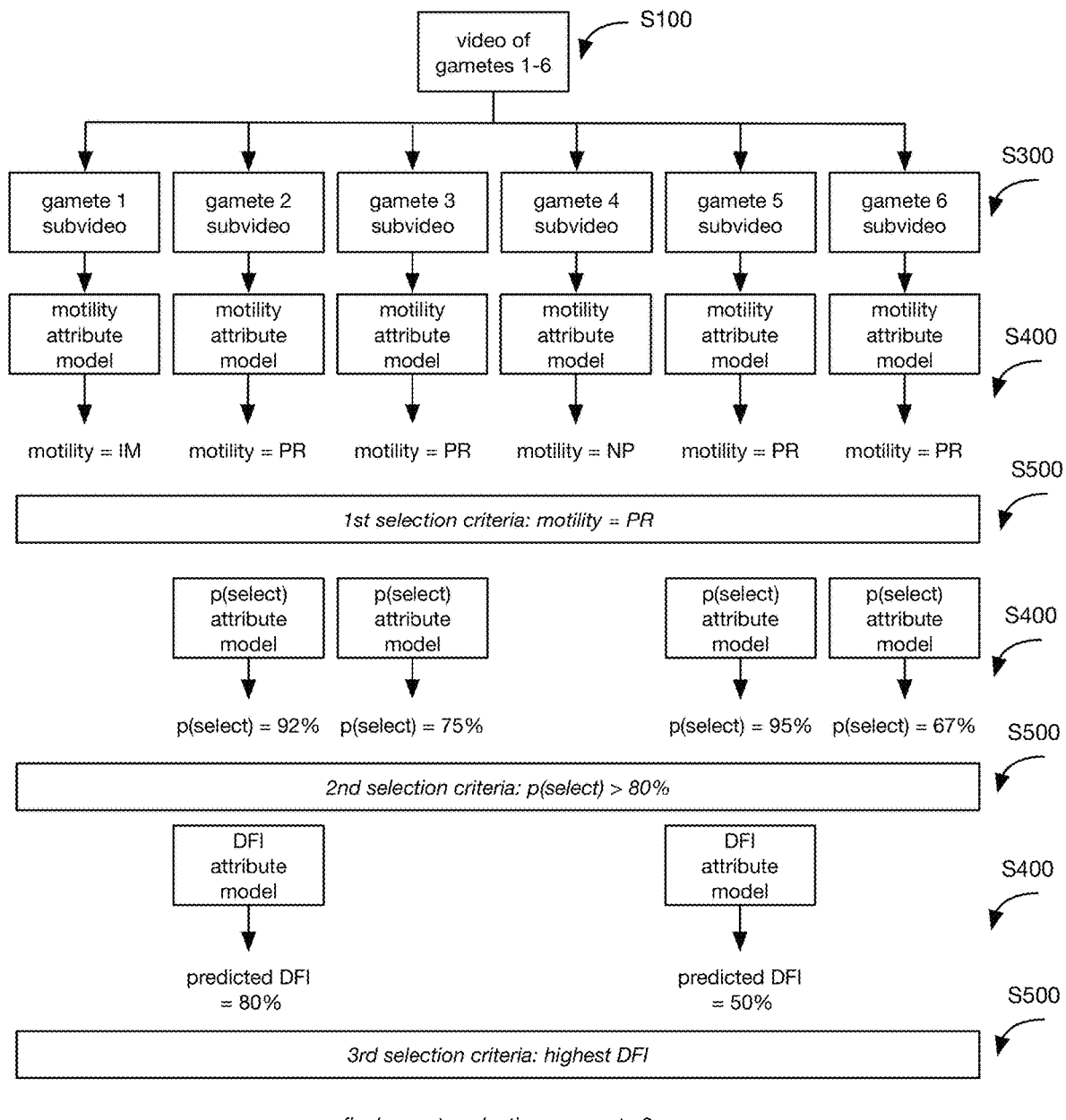
FIG. 11 depicts a first illustrative example of selecting a gamete.

In a first illustrative example of this variant, a motility and/or morphology attribute value can be determined for each gamete using a first attribute model (e.g., a kinematic model, a classifier, etc.). The gametes can be filtered (e.g., a pre-filter) to generate a first subset of gametes classified with a mobility classification above a threshold (e.g., "progressively motile"). For each gamete in the first subset, a trained gamete attribute model can be used to predict a selection metric. A second filtering step can then be used to generate a second subset of gametes with a selection metric greater than a threshold (e.g., a probability of selection>80%). For each gamete in the second subset, another trained gamete attribute model can be used to predict a DFI attribute value. One or more gametes can then be selected (e.g., a post-filter) from the second subset based on a comparison between DFI attribute values (e.g., the highest DFI attribute value is selected). An example is shown in FIG. 11.

Figure 12:
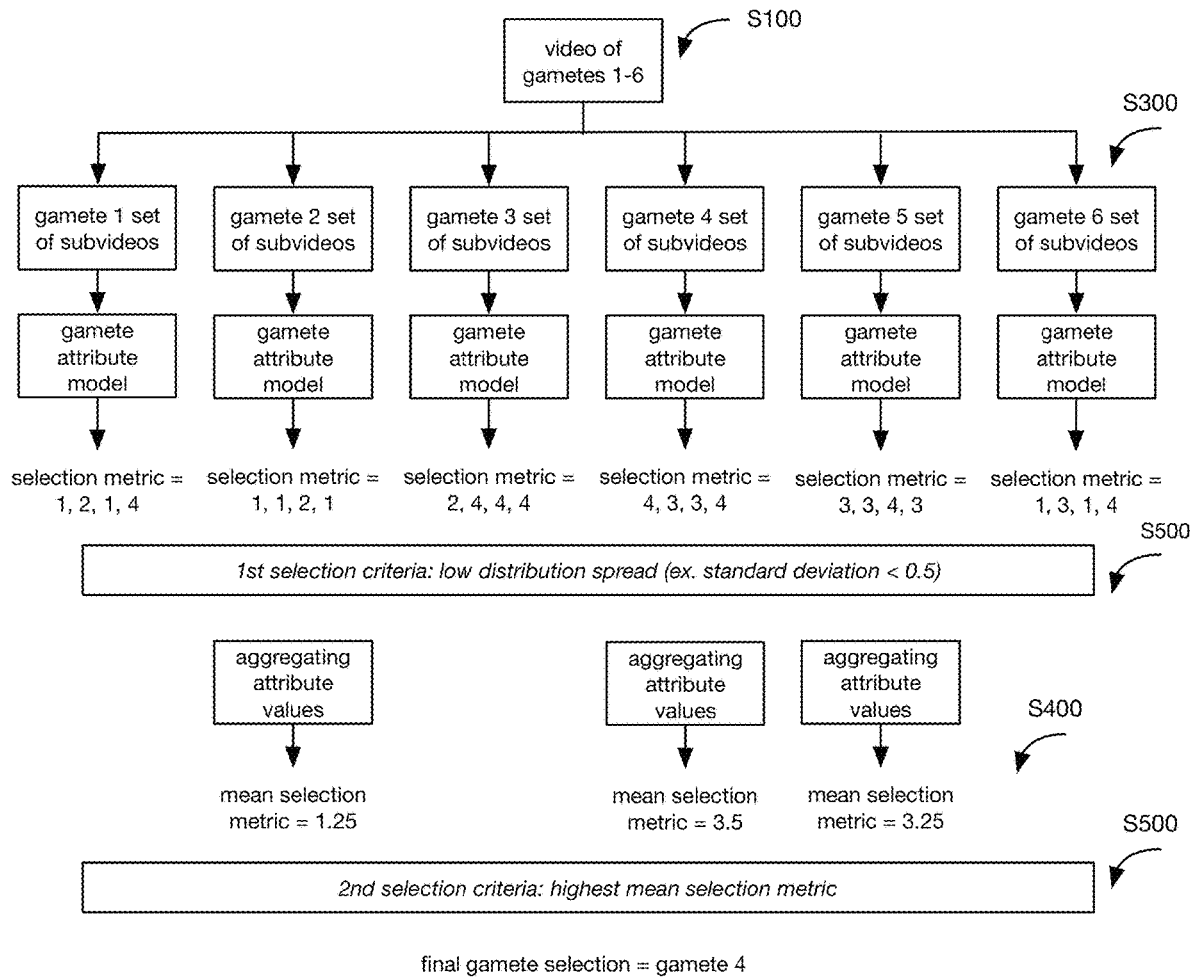
FIG. 12 depicts a second illustrative example of selecting a gamete.

In a second illustrative example of this variant, selection metrics can be determined for each gamete across a series of sub-videos using a trained gamete attribute model. The gametes can be filtered to generate a subset of gametes with a selection metric distribution standard deviation less than a threshold. One or more gametes can then be selected from the subset based on a comparison between selection metrics (e.g., the gamete with the highest mean selection metric is selected). An example is shown in FIG. 12.

In a tenth variant, the gamete can be selected using the retrieval system (e.g., physical selection and/or isolation). This variant can be performed: randomly, based on motility, based on density (e.g., be the gametes within a centrifuged pellet), and/or otherwise selected. In a first embodiment, a gamete subpopulation is selected using density gradient centrifugation, swim up, sperm washing, and/or other sperm selection techniques. In a second embodiment, the gamete is individually selected and aspirated by the retrieval system (S600). In a third embodiment, the gametes are individually isolated using cell sorting. In a fourth embodiment, the gametes are selected using a combination of the aforementioned methods. For example, a high-motility gamete subpopulation can be isolated from the gamete sample using the first embodiment, wherein individual gametes can be isolated from the selected gamete subpopulation.

However, the gamete can be otherwise selected.

S500 can be performed once, iteratively performed, or performed any number of times.

In a first variant, S500 is performed once. In this variant, attribute values for a set of gametes are extracted from the video, wherein a subset of gametes are selected based on the respective attribute values. For example, gametes can be selected after: attribute values have been collected for a predetermined number of evaluation epochs, after a threshold number of gametes have been evaluated, and/or when any other condition is met.

Figure 13:
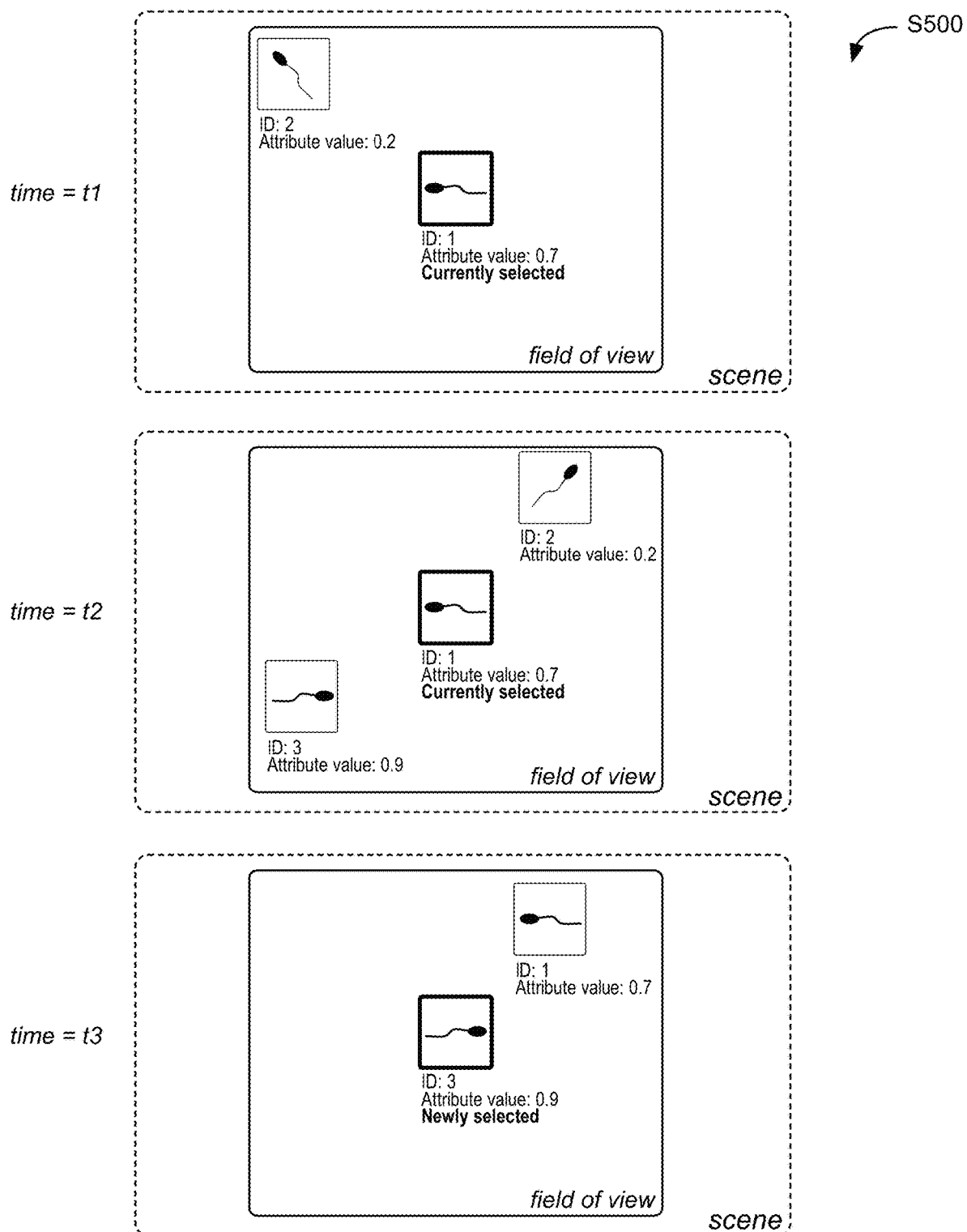
FIG. 13 depicts an illustrative example of replacing a gamete selection.

In a second variant, S500 is iteratively performed. In this variant, a first gamete is selected from a first sub-population of gametes visible in a first set of sub-videos (e.g., using one or more of the selection variants discussed above). The imaging system is preferably static relative to the scene while the first set of sub-videos are being recorded, but can alternatively move relative to the scene. The first gamete is then tracked (e.g., across the physical scene, to a new scene segment, etc.), wherein attribute values are determined for new gametes appearing in the field of view. A second gamete can be selected (e.g., instead of the first gamete, to replace the first gamete, etc.) when the second gamete's values (e.g., individual values, aggregate values, etc.) satisfy the selection criteria better than the first gamete's (e.g., example shown in FIG. 13). The method can then be iteratively repeated until a stop condition is met. Examples of stop conditions can include: a predetermined time duration is met, the same gamete or no new gametes been selected for a predetermined number of epochs, the selected gamete's attribute values satisfy a predetermined set of conditions, a user manually selects the selected gamete, a statistical measure of the second gamete's attribute value distribution better satisfies a selection criteria as compared to the first gamete's attribute value distribution, after a threshold number of gametes have been evaluated, and/or any other stop condition.

However, S500 can be repeated or not repeated in any other suitable manner.

S500 can concurrently select a single gamete or multiple gametes. When multiple gametes are selected, the system can track each gamete through the scene (e.g., using the same imaging system or a different imaging system with a wider field of view); track each gamete as long as they remain within the imaging system's field of view, then select a subset of gametes to track when they begin to spatially diverge; and/or otherwise track the multiple selected gametes. However, any other number of gametes can be concurrently, contemporaneously, or asynchronously selected.

However, the gamete can be otherwise selected.

The method can optionally include explaining the gamete selection S550, which can function to output semantic information related to a given gamete attribute model output. S550 can be performed after S500, after S700, during S400 (e.g., where S550 is used to determine an attribute value), and/or at any other time.

In a first variant, explaining the gamete selection can be based on other attribute values output by the gamete attribute model. For example, the gamete attribute model can be trained to output values for multiple attributes (e.g., in addition to the attribute values used for gamete selection in S500). The additional attribute values can provide additional context for the attribute values used in gamete selection and/or for the selection itself.

In a second variant, the gamete attribute model can be introspected using explainability methods. In a first example, features can be extracted and/or analyzed from the gamete attribute model (e.g., using SHAP values, feature importance and/or weights, partial dependency, feature interaction, accumulated local effects, LOCO, permutation impact, LIME, etc.). In a first specific example, nonsemantic features of high importance can be identified, wherein a second model can be used to convert the identified features to a semantic parameter (e.g., a morphology and/or motility attribute value). In a second specific example, semantic features of high importance can be identified and directly translated to a semantic parameter. In a second example, an (interpretable) surrogate model can be used to determine semantic parameters. An example is shown in FIG. 10.

In a first illustrative example, the gamete attribute model is a black box model trained to output a selection metric based on the video. An explainability analysis is used to interpret a low selection metric for a given gamete, outputting a morphology attribute value that indicates abnormal head shape (e.g., where abnormal head shape is thus a likely cause of the low selection metric). In a second illustrative example, determining a morphology attribute value and/or a motility attribute value includes extracting explainability values from the model, wherein the morphology attribute value and/or the motility attribute value are determined based on the explainability values.

Explaining the gamete selection can additionally or alternatively include storing (e.g., in a database): a video, sub-video, attribute values, model version identifier, and/or any other information, wherein the information can be further analyzed (e.g., manually analyzed), used to train or refine the models, and/or otherwise used.

However, the gamete selection and/or gamete attribute model can be otherwise analyzed.

The method can optionally include facilitating physical gamete retrieval S600, which can function to physically isolate the selected gamete(s) for further processing. Further processing can include: using the gamete for in vitro fertilization (IVF), intracytoplasmic sperm injection (ICSI), intracytoplasmic morphologically selected sperm injection (IMSI), other assistive reproductive technologies (ART), storing the gamete (e.g., freezing the gamete, such as for in vitro fertilization), using the gamete to generate additional training data and/or attribute values, for animal husbandry, for cell culture, and/or any other suitable process. For example, the selected gamete can be used in IVF, wherein a selected spermatozoon can be inserted into an ovum. In another example, one or more selected spermatozoa can be collocated with one or more ovum in a controlled environment (e.g., in a well, etc.). S600 can be performed by a retrieval system, which can be or augment a retrieval agent. The retrieval agent can be: a human, the retrieval system, and/or any other suitable agent. S600 can be performed after S500, after S500 has a predetermined confidence level, and/or at any other suitable time. S600 is preferably performed in real time, but can be performed at any time.

In a first variant, the retrieval system can include an augmented reality system (e.g., headset; microscope overlay; gimbal mounted to a bench; screen; etc.), wherein a bounding box or other selected gamete indicator is overlaid over a real-time image of the scene to facilitate easier manual retrieval. The overlay can optionally include auxiliary information, such as gamete identifier, gamete attribute values, and/or other information (e.g., shown by default or toggled on by the operator). For example, the microscope can be modified such that the overlay generated by the method is displayed on a small LCD display, which will then be projected in the light path using special optics. This will enable specialists to view the selection recommendation directly from the microscope eyepiece.

In a second variant, the retrieval system includes a robot (e.g., with an aspirator, suction end effector, ICSI needle, cell sorter, etc.) that automatically tracks and retrieves the selected gamete. In a specific example, once the gamete is selected, the scene and/or robot arm can be dynamically moved to keep the selected gamete within the robot or camera's field of view and/or within the robot's active area.

The robot can then aspirate, immobilize (e.g., by cutting off the sperm's tail), micromanipulate, and/or otherwise manipulate the selected gamete.

In a third variant, the system can recommend one or more gamete candidates, present the gamete candidates to a user (e.g., professional, operator, etc.) for approval, and control a robot to automatically facilitate retrieval of the selected gametes. Presenting the gamete candidates to the user can include: presenting a video identifying the gamete candidate (e.g., with a bounding box, highlighted, etc.) to the user; presenting the gamete parameter values to the user; providing an overlay (e.g., selected gamete indicator) over a view of the scene in real- or near-real time; and/or otherwise presenting the gamete candidates to the user.

However, any other suitable retrieval system can be used.

The method can optionally include training one or more models to predict the attribute values for a gamete S700, which can function to generate gamete attribute models and/or update the gamete attribute model to improve gamete selection. S700 can be performed after S300, prior to S400, after S500 (e.g., where gametes are selected based on a low confidence score for model feedback), and/or at any other time. S700 can be performed remotely from the imaging system, but can alternatively be performed locally to the imaging system (e.g., where the imaging system is the same as the imaging system used to sample videos S100 for gamete selection or a different imaging system). The gamete (e.g., a training gamete in a set of training gametes) used in S700 is preferably a different gamete from that used in S100-S500, but can additionally or alternatively be the same.

S700 can be iteratively repeated for a single gamete, iteratively repeated for a set of gametes, performed in response to a trigger (e.g., in response to a user validating and/or adjusting a gamete selection and/or gamete attribute value), and/or be otherwise performed. Iteratively repeating S700 can function to acquire multiple attribute values for a single gamete, which can decrease individual bias, increase a prediction attribute value's confidence level, and/or otherwise improve model training. In a first example, the same gamete and associated information (e.g., image, video, sub-video, gamete track, etc.) are provided to each specialist in the specialist set for labeling. In a second example, the same gamete is associated with multiple sets of information (e.g., multiple videos), where each set of information is provided to a specialist for labeling. In a third example, S700 is repeated for different gametes in a set. In a fourth example, S700 is iteratively performed for the same gamete to train different gamete attribute models (e.g., corresponding to different gamete attributes). In a specific example, the same gamete and/or the same associated information (e.g., a sub-video of the gamete) can be used to train a selection metric model and to train a DFI attribute model. In a fifth example, S700 is iteratively performed for different gametes to train different gamete attribute models, where each model is trained on a different gamete set.

S700 can include: sampling a video of a gamete, optionally tracking the gamete across successive images, optionally determining a sub-video depicting the gamete, determining training attribute values for the gamete (e.g., where the attributes are those described in S400), and training the gamete attribute model to predict the training attribute values for the gamete (e.g., where the trained model is used in S400).

Sampling the video of the gamete, optionally tracking the gamete across successive images, and optionally determining a sub-video depicting the gamete (performed as part of S700) are preferably the same methods as detailed in S100, S200, and S300, respectively. However, the methods can be different. For example, the video sampled during S700 (e.g., for specialist labelling, to generate data associated with training attribute values for model training, etc.) can depict the gamete in a sample prepared with motility retardant (e.g., wherein the gamete is immersed in a solution with motility retardant), while the video sampled during S100 can depict the gamete in a sample without motility retardant. In this example, when the attribute values are predicted for gametes prepared without motility retardant (e.g., gametes in the S100 video are not in motility retardant), S700 can include: sampling a first video of a gamete without motility retardant (e.g., such that the first video has the same video parameters as the S100 video), sampling a second video of the gamete in motility retardant, determining the training values for the gamete based on the second video, optionally associating the training values with the same gamete identified in the first video, and training the models to predict the training values for the gamete based on the first video. Additionally or alternatively, in this example, the model can be trained to ingest appearance features extracted from the motility-retarded video and/or motility features extracted from the first video. However, the model can be otherwise trained when the videos are not the same.

Determining training attribute values (e.g., actual values, ground truth values, etc.) functions to determine a training target for the gamete. Examples of training attribute values include: labels (e.g., classifications, scores, etc.), measurements, and/or any other type of value. One or more training attribute values for the same or different gamete attribute can be determined for each gamete (e.g., training gamete), using one or more instances of the same or different method. The training attribute values can be: manually determined (e.g., by a specialist), calculated (e.g., using measurements, using slower models than that used in inference, etc.), and/or otherwise determined.

In a first variant, the training attribute values are labels received from a user (e.g., a specialist). In a first example, gathering manual labels includes providing one or more images, videos, and/or sub-videos depicting a gamete to a specialist, then receiving one or more gamete labels from the specialist, wherein the gamete attribute values can be the labels and/or be determined from the labels (e.g., a label of "borderline healthy" corresponds to an attribute value of 3). In a second example, gathering manual labels includes displaying gametes (e.g., by an imaging system in real-time, in a video, etc.) with their corresponding attribute values determined (e.g., using S400). The specialist can then manually confirm and/or adjust the determined attribute values (e.g., by providing a corrected gamete label). However, manual labels can be otherwise determined.

Labels can include: an overall rating, a selection value, motility attribute values, morphology attribute values, and/or any other qualitative or quantitative gamete evaluation. Qualitative labels can optionally be converted to quantitative labels (e.g., based on a predetermined mapping, etc.). The labels can be used for gamete selection (e.g., as a selection metric) or be otherwise used The overall rating label can be a number on a quantitative scale (e.g., the gamete is rated on a scale from 1-4), a classification (e.g., unhealthy, borderline unhealthy, borderline healthy, and healthy), and/or any other attribute value. Additionally or alternatively, the overall rating can be a combination of specialist labels (e.g., calculated based on motility attribute value labels and morphology attribute value labels).

The selection label can be a selection rating and/or score (e.g., on a scale from 1-5), selection ranking, likelihood of selection, binary classification (e.g., select or do not select), actual physical selection of the gamete, and/or any other attribute value. For example, one or more candidate gametes can be ranked by the specialist in order of selection preference, wherein the selection label can be a score calculated based on the provided rank (e.g., using the ELO rating method, Harkness rating method, or other rating method). In another example, the specialist can assign the selection label based on whether they would select the gamete for use in assistive reproduction (e.g., assign a binary yes/no label).

Motility attribute value labels are preferably ontological classes (e.g., WHO classifications), but can alternatively be scores, a set of quantitative parameters, and/or any other attribute value. Examples of ontological mobility classes can include: progressively motile (PR), non-progressively motile (NP), and immotile (IM); grades a, b, c, and d; rapid and slow; and/or any other mobility class. In another example, the overall gamete motility can be classified on a discrete or continuous numeric scale (e.g., scale of 1-5, 1-10, etc.).

Morphology attribute value labels are preferably ontological classes (e.g., WHO classifications), but can alternatively be scores, a set of quantitative parameters, and/or any other attribute value. Morphology attribute values can be determined for: the gamete as a whole, components of the gamete (e.g., head, neck, midpiece, tail, etc.), and/or any other suitable portion of the gamete. Each gamete component preferably has a single classification, but can alternatively have multiple classifications. In a first example, the gamete head can be classified as: normal, large, small, tapered (elongated), pyriform (pear shaped), round, amorphous (constricted), vacuolated, small acrosomal area (<40% of the head area), double head, no acrosome globozoospermia (head appears small and sound due to the failure of acrosome to develop), detached, out of focus, any combination thereof, and/or have other classifications. In a second example, the neck and midpiece can be classified as: normal, bent neck, asymmetric (asymmetrical insertion of midpiece into the head), irregular, thick (thick insertion), thin (thin insertion), bent, cytoplasmic droplet, any combination thereof, and/or have other classifications. In a third example, the tail can be classified as: normal, short, multiple, hairpin, broken, bent, coiled, terminal droplet, irregular width (e.g., thick), any combination thereof, and/or have other classifications. In a fourth example, the cytoplasm can be classified as: normal, excess cytoplasm (e.g., >⅓ of the head size), irregular cytoplasm, any combination thereof, and/or have other classifications. In a fifth example, the overall gamete morphology can be classified on a discrete or continuous numeric scale (e.g., scale of 1-5, 1-10, etc.).

However, any other manual label can be received from a user (e.g., specialist).

A label can optionally be normalized based on one or more previous labels provided by the same specialist. This can accommodate for specialist-specific preferences and/or other biases. In a first embodiment, the label can be normalized with respect to labels assigned by the specialist to one or more reference gametes. In a second embodiment, the label can be normalized with respect to an aggregated set of labels assigned by the specialist to each gamete in a set. In a third embodiment, the label can be normalized with respect to aggregated labels for the same gamete from other specialists in the specialist set. For example, a first specialist's selection metric might be corrected upward when the first specialist is more conservative than their colleagues (e.g., consistently assign lower selection metrics for the same gamete; mark less gametes as selectable; etc.). However, a label can be otherwise normalized and/or not be normalized.

Specialist weighting of different gamete attributes can optionally be determined from the labels provided by the same specialist. The specialist weighting can be used to determine the model's weight for the respective attribute, used to select attributes to explain a gamete selection, used to unbias the model (e.g., identify that the training data is biased in that manner, and ignore or otherwise manage said attribute), and/or otherwise used. The specialist weighting can be: manually specified by the specialist, learned from the specialist's labels, or otherwise determined. Learning the specialist weighting from the specialist's labels can include: determining a correlation between gamete selection by the specialist and each gamete attribute (e.g., using a regression, etc.); training a model (e.g., the same or different model as the gamete attribute model) to predict specialist selection based on the gamete attribute values, and extracting the weights associated with each gamete attribute; and/or otherwise determined.

Labels can optionally be aggregated across specialists in the set to determine a training gamete attribute value.

In a first embodiment of label aggregation, a selection probability for a gamete (e.g., representing the probability that a specialist would select the gamete for use in assistive reproduction) can be determined by aggregating selection metrics. In a first example, each specialist in the set assigns a binary "select" or "do not select" label to a gamete (e.g., based on a video or sub-video of the gamete, wherein the same video or sub-video is provided to each specialist). A selection probability for the gamete can then be calculated based on the binary labels (e.g., where the selection probability is 80% when 80% of the specialists in the set choose the "select" label). In a second example, each specialist in the set assigns a likelihood that they would select that gamete. The aggregated likelihoods for each specialist can determine an overall selection probability for the gamete. In a third example, each specialist in the set assigns a selection rating to the gamete. The aggregated selection rating (e.g., average selection rating) can be converted to a selection probability using an equation (e.g., an average selection rating of 8 converts to a 60% selection probability), using previous selection results, and/or using any other conversion method. In a fourth example, each specialist in the set assigns a ranking to the gamete when compared to one or more other candidate gametes. The aggregated rankings for the gamete across the specialists can determine an overall selection probability for the gamete (e.g., a probability that the gamete would "win" when ranked with the other candidate gametes). In a fifth example, each specialist in the set assigns one or more selection metrics (e.g., a morphology attribute value label, a motility attribute value label, etc.), wherein the selection or success probability (e.g., also received from the specialist, determined from development data, etc.) can be determined (e.g., calculated, predicted, etc.) based on the one or more selection metrics.

Figure 8:
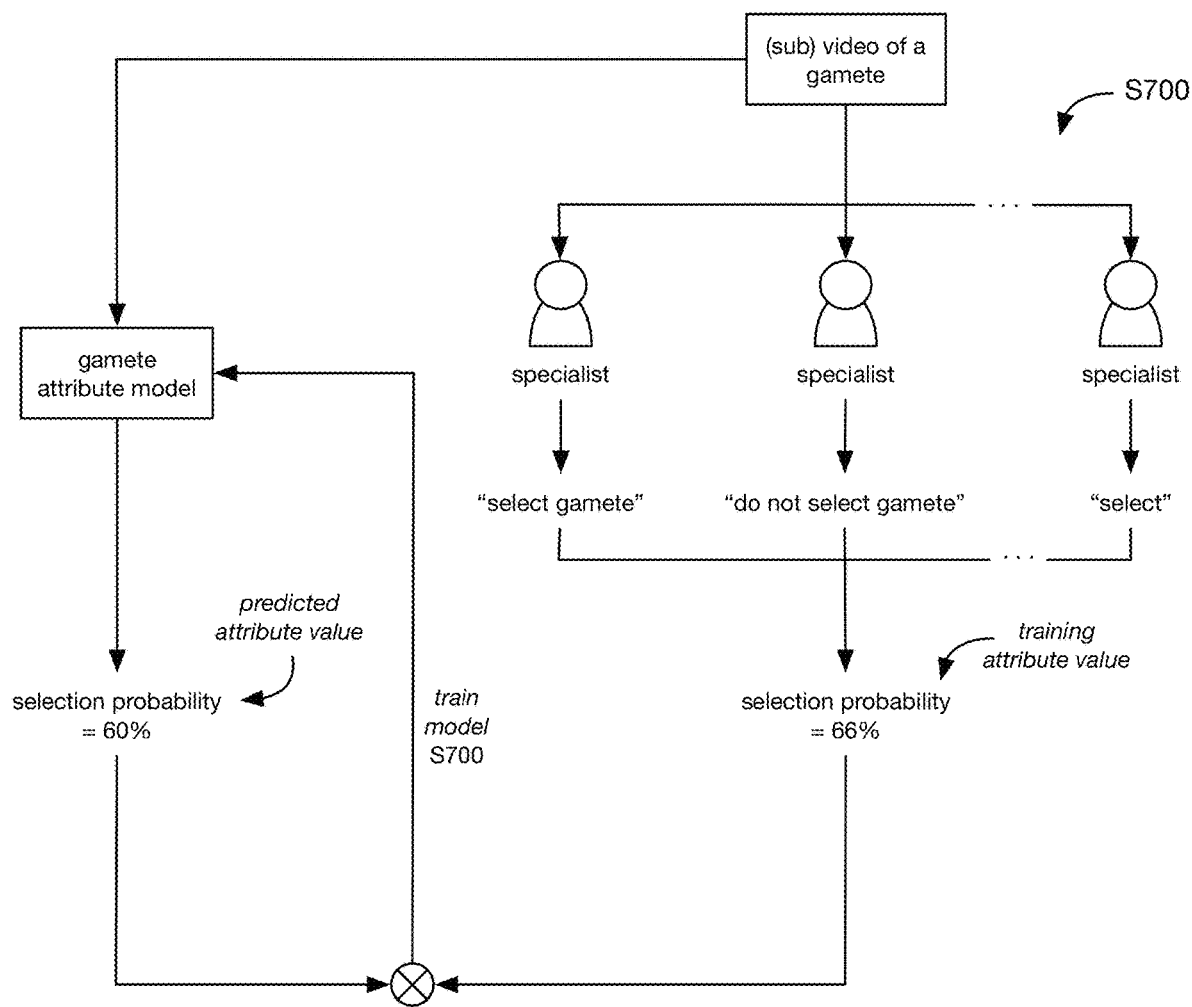
FIG. 8 depicts an illustrative example of training a gamete attribute model to predict a selection probability.

In an illustrative example of the first embodiment, S700 includes: sampling a video of a set of gametes; tracking an individual gamete in the set; extracting a sub-video of the individual gamete from the video; providing the sub-video to a set of specialists; from each specialist in the set, receiving a selection metric for the individual gamete; determining a selection probability for the individual gamete based on the selection metric received from each embryologist in the set; and training a model to predict the selection probability for the individual gamete based on the sub-video (e.g., example is shown in FIG. 8).

In a second embodiment of label aggregation, an attribute value can be calculated for a gamete by averaging (e.g., using a weighted average) labels across the specialists. In this embodiment, the labels can be quantitative labels and/or qualitative labels converted to quantitative labels.

In a third embodiment of label aggregation, a label from a specialist can be treated as a vote, wherein the attribute value can be determined based on the label votes. For example, the attribute value with the majority, supermajority, and/or any other suitable proportion of votes can be treated as the attribute value.

In a fourth embodiment of label aggregation, a distribution of labels for a gamete can be determined from the specialist labels. In a first example, the attribute value can be the label distribution itself. In a second example, the attribute value can be statistical measure of the distribution. In a third example, a confidence score (e.g., a statistical measure of the distribution) can be associated with the gamete attribute value (e.g., wherein the attribute value is the average of the labels). The confidence score can be used to weight and/or select data for model training. In an illustrative example, a high distribution spread (e.g., little agreement between specialists) can result in a low confidence score, which can be used to decrease the influence of the associated data in model training (e.g., the gamete sub-video and/or training attribute values are weighted lower and/or not used for model training).

In a second variant of determining training attribute values for the gamete, the training attribute values are measured attribute values for the gamete prior to fertilizing the gamete and/or without fertilizing the gamete. The attribute values can be measured using destructive and/or nondestructive techniques.

Gamete attribute values measured using destructive techniques (e.g., destructive attribute values) preferably includes information that can conventionally only be obtained by physically compromising the gamete in some manner (e.g., by lysing, staining, disrupting, or otherwise physically changing the specimen), but can be an internal parameter or be otherwise defined. In variants, training a gamete attribute model to infer destructive attribute values from noninvasive measurements of a gamete (e.g., videos) can leave the gamete intact, such that the gamete can be used in downstream fertility processes (e.g., for IVF), while enabling previously-unobtainable information (information that would have otherwise required gamete destruction) to be considered in the downstream fertility process.

Destructive attribute values can include: DNA fragmentation index (DFI), gene analysis (e.g., from PCR or other DNA or RNA analyses), DNA condensation level, biochemical marker analysis, chromatin levels, acrosome thickness, acrosome mass, mitochondria parameters (e.g., concentration, number, volume, etc.), centriole parameters (e.g., centriole structure, centriole density, etc.), vitality and/or any other information.

The destructive attribute values can be determined using a staining technique (e.g., DFI technique, vitality techniques, etc.), PCR, flow cytometry, and/or other destructive techniques. Examples of DFI techniques that can be used include: the acridine orange test (AO), sperm chromatin structure assay (SCSA), deoxynucleotidyl transferase-mediated dUTP nick end labeling assay (TUNEL) (e.g., by flow cytometry or light microscopy), the single-cell gel electrophoresis assay (COMET), the sperm chromatin dispersion test (SCD, e.g., Halosperm™), flow cytometry, and/or other DFI methods. Examples of vitality tests can include: eosin-nigrosin, eosin alone, hypo-osmotic swelling, and/or any other method. However, any other suitable staining and/or destructive methods can be used.

Figure 6:
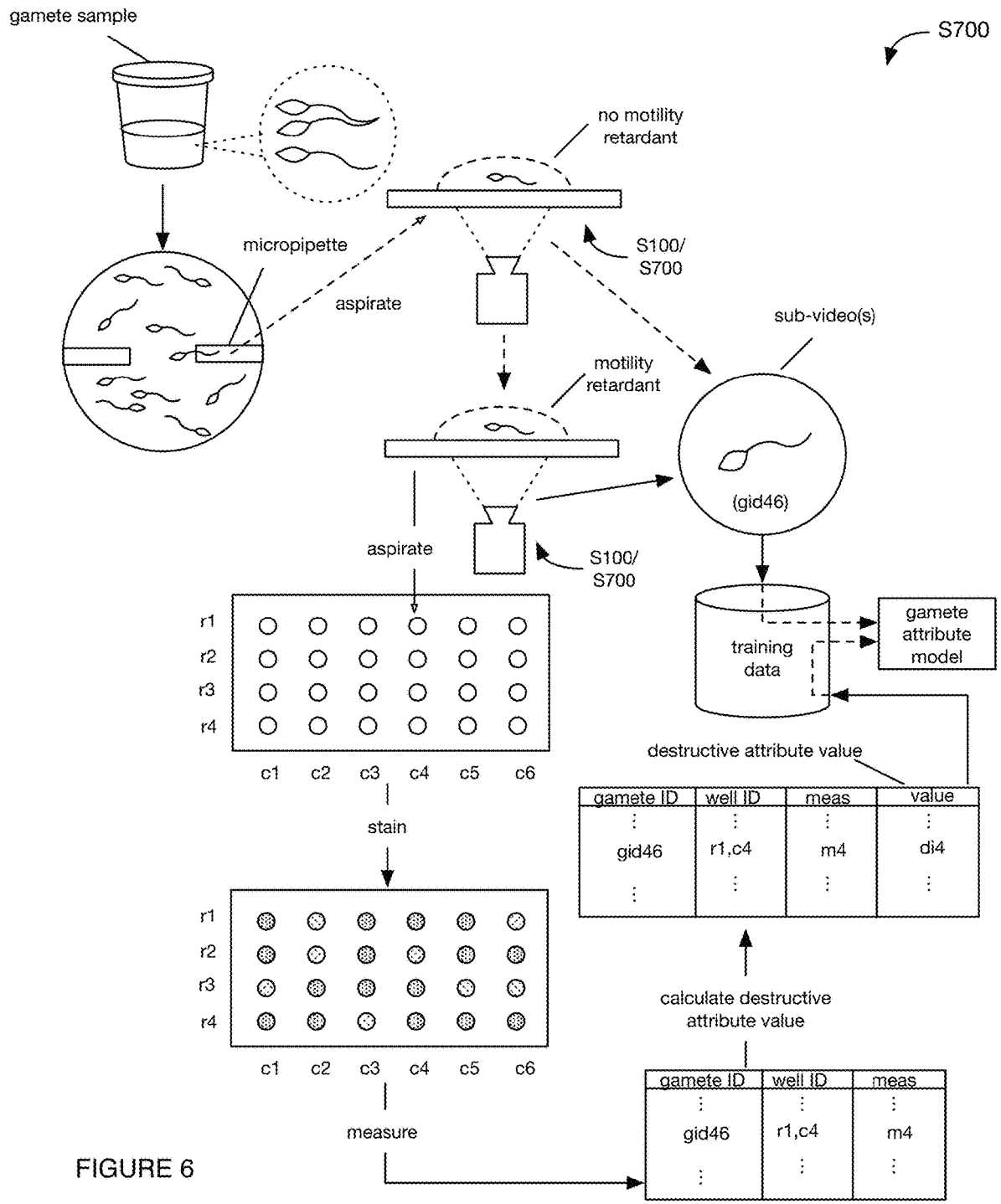
FIG. 6 depicts an illustrative example of determining a destructive attribute value.

In an example, S700 includes: selecting an individual gamete from a gamete sample; optionally assigning the gamete a unique gamete identifier; optionally immersing the gamete within a motility retardant; sampling video of the gamete; destructively analyzing the gamete (e.g., fixing and staining the gamete); determining an training attribute value (e.g., DFI value) for the gamete based on the destructive analysis; optionally repeating the above process for a plurality of gametes; and training the gamete attribute model (e.g., regression model) using the videos and training attribute values for each gamete. The video can be sampled before, after, and/or both before and after gamete isolation and/or immersion within the motility retardant, wherein the model can be trained using the pre-isolation or pre-immersion video, the post-isolation or post-immersion video, and/or both. An example is shown in FIG. 6.

In a first specific example, S700 includes: loading individual gametes (e.g., selected in S500) into individual wells prepared with an adhesion agent (e.g., poly-L-lysine, etc.); recording the gamete identifier for the gamete in each well; fixing the gametes within the wells; staining the gametes within the wells; measuring the gamete fluorescence (e.g., wherein the well is excited with a single frequency or narrow frequency band, such as 450-490 nm; wherein the well is excited with a wide set of frequencies; etc.); and calculating the destructive attribute values (e.g., DFI value) based on the measured fluorescence.

In a second specific example, S700 includes: suspending the gamete in fluid; staining the gamete; flowing the gamete through a flow cytometer; sampling the stain measurement for the gamete, as the gamete flows through the flow cytometer; optionally concurrently sampling a secondary noninvasive measurement (e.g., for gamete association), and calculating the destructive attribute values (e.g., DFI value) based on the stain measurement.

In a third specific example, S700 includes: lysing a gamete, isolating the DNA for the gamete (e.g., by centrifuging the lysed solution), running an assay on the isolated DNA, and calculating the destructive attribute values (e.g., gene parameter) from the assay results.

However, training attribute values can be otherwise experimentally determined.

In a third variant of determining training attribute values for the gamete, the training attribute values are measured attribute values (e.g., development data) for the gamete after fertilizing the gamete (e.g., including successful or unsuccessful gamete fertilization). Development data can include preimplantation genetic testing-aneuploidy (PGT-A), Preimplantation genetic testing-monogenic (PGT-M), preimplantation genetic testing-structural rearrangements (PGT-SR), chorionic villus sampling, amniocentesis, DNA sequencing, blastocyst formation (e.g., euploid blastocyst formation), blastulation rate, blastocyst grading, cleavage stage embryo grading, fertilization success (e.g., a binary success metric), implantation success, pregnancy stage success (e.g., a success metric at each pregnancy stage), live birth success, miscarriage occurrence, and/or any other data acquired during or after fertilization using the gamete. The development data can be determined by tracking the pregnancy and birth associated with a given gamete, and/or otherwise determined.

In a fourth variant of determining training attribute values for the gamete, the training attribute values can be calculated using classical or traditional models as described in S400.

Multiple attribute values for a single gamete can be used for model training. In a first variant, a specialist determines training attribute values for each of a set of gamete attributes (e.g., head defects, neck defects, midpiece defects, tail defects, excess residual cytoplasm, motility, a selection value, etc.). The set of training attribute values for the gamete can then be used for training one or more gamete attribute models. In a second variant, a specialist determines training attribute values for a subset of gamete attributes (e.g., only a selection value). This subset can be supplemented with calculated gamete attribute values (e.g., calculated morphology and motility attributes using a classical or traditional model as described in S400), measured attribute values, and/or not be supplemented with additional attribute values. Training attribute values can optionally be aggregated (e.g., to form a combined attribute value) as described in S450.

Training the gamete attribute model can include associating the training attribute values with training inputs (e.g., collectively, "training data"), and training the model to predict the training attribute value based on the training inputs. The training inputs can include: a video, sub-video, image, a gamete track, features extracted therefrom, any combination thereof, and/or any other measurable gamete data. The training attribute values are preferably associated with the training inputs using a gamete identifier, but can alternatively be associated based on a known association between a specialist label and the gamete identifier, a known association between the test well and the gamete identifier, a shared method instance, shared features, and/or otherwise determined.

In a first variant, the method is serially performed (e.g., performed for a single gamete before it is repeated for the next gamete). In this variant, the training attribute values determined in S700 are associated with the training data determined in the same (shared) method instance (e.g., where the training data is acquired prior to the training attribute values).

In a second variant, the training attribute values and training inputs are associated via a common gamete identifier (e.g., automatically or manually assigned to the gamete).

In a third variant, the training attribute values and training inputs are associated via shared features. In this variant, features can be extracted from two separate training input instances (e.g., two videos) sampled during S700, wherein the attribute values and the training data are associated when the respective features are matched (or similar within a predetermined threshold). For example, appearance features can be extracted from a video of the unstained gamete, and appearance features can be extracted from an image of the stained gamete. The video (e.g., the training data) can be associated with the gamete attribute values determined from the stain measurements when the appearance features substantially match.

However, the training attribute values can be otherwise matched with the training data.

The gamete attribute model is preferably trained on multiple matched pairs of training inputs and training attribute values (e.g., from multiple gametes), but can alternatively be trained on a single pair of training data and attribute values for a single gamete (e.g., using single-shot training). The model can be trained on 1,000, 10,000, 100,000, 1 million, and/or any other suitable number of pairs of training data and attribute values. The inputs for model training are preferably the training inputs for each gamete, but can additionally or alternatively include: population data (e.g., wherein the average gamete attribute value, spread for the gamete attribute, and/or other population analysis is provided as an input), training attribute values for other gametes, and/or other information. Examples of training inputs can include: a video, a sub-video, an image, a gamete model (e.g., geometric model, 3D model, etc.), a gamete track, electromagnetic response information, acoustic information, impedance, reflectance, rigidity, features extracted therefrom, any combination thereof, and/or other gamete information. The training inputs are preferably noninvasive data acquired for the gamete, but can alternatively include invasive data. The targets for model training are preferably the training attribute values associated with the training input, but can be other information.

However, the gamete attribute model can be otherwise trained.

The method can optionally include generating population-level analyses S800, which can function to provide batch analytics for a gamete population (e.g., from a patient). The population-level analyses can be determined based on: S200 (e.g., the number of gametes, gamete features, a gamete track, etc.); S400 and/or S700 (e.g., attribute values); a slide-level scan (e.g., using the motorized stage); measurements; and/or other processes. The population-level analysis can be generated using data (e.g., attribute values) for all or a plurality of gametes in a sample, for all or a plurality of gametes identified in the sample, for all or a plurality of gametes in a field of view, for the sample; and/or for any other gamete population. The analysis can be relative to a reference population (e.g., the sample from which a gamete was derived, a previous sample, an average sample, etc.). In an example, a given gamete in a sample has an attribute value that is one standard deviation above the mean relative to the attribute values of a reference population.

Population-level analyses can include a statistical measure (e.g., mean, median, standard deviation, spread, etc.), an aggregation, a percentage (e.g., percent of gametes above a threshold), count, ratio, and/or any other analysis of gamete data. The gamete data can include: gamete count (e.g., of all gametes, of motile gametes, etc.), gamete concentration, gamete attribute values (e.g., motility, morphology, DFI, selection probability, etc.), gamete viability, seminal fluid measurements (e.g., composition, pH, etc.), sample volume, sample weight, contaminant parameters (e.g., presence, class, amount, prevalence, and/or other parameter for blood, bacteria, and/or other contaminants), and/or other gamete data. In a first variant, the gamete data can be determined manually, wherein a user manually classifies and/or counts the gametes. In a second variant, the gamete data can be determined automatically using a sensor (e.g., camera, transceiver, etc.). For example, an image of the sample (e.g., on a slide) can be captured and analyzed (e.g., using an object detector, an optical flow model, using the gamete attribute model, etc.) to extract the gamete data.

In specific examples, a population-level analysis based on motility can include: overall motility (e.g., percent of sperm showing any movement), rapid motility (e.g., percent of sperm traveling at a speed of 25 um/sec or faster), linearity (e.g., percent of sperm moving in a straight line path), progressive motility (e.g., percent of sperm moving rapidly and in a straight path), mean velocities (an average speed for all sperm in the field of view), amplitude of lateral head displacement (e.g., the average distance that the sperm head shifts back and forth while moving). In another specific example, a population-level analysis can be the percent of gametes in a sample with a given attribute value greater than a threshold (e.g., a predetermined viability threshold).

However, population-level analysis can be otherwise defined.

Alternative embodiments implement the above methods and/or processing modules in non-transitory computer-readable media, storing computer-readable instructions, that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
    sampling a video of a gamete;
    automatically determining a gamete attribute value for the gamete based on the video, using a trained model; and
    automatically determining a confidence parameter for the gamete attribute value based on the video;
    wherein the gamete is selected from a set of gametes based the gamete attribute value and the confidence parameter.

2. The method of claim 1, wherein the gamete attribute value is one of a set of gamete attribute values determined based on the video using the trained model, wherein each gamete value in the set corresponds to a different timestamp in a timeseries, wherein the gamete is selected based on the set of gamete attribute values.

3. The method of claim 2, further comprising aggregating gamete attribute values in the set of gamete attribute values, wherein the confidence parameter is determined based on the aggregated gamete attribute values.

4. The method of claim 1, further comprising determining a second gamete attribute value based on the video, wherein the confidence parameter is determined based on the gamete attribute value and the second gamete attribute value.

5. The method of claim 4, wherein the second gamete attribute value is determined using the trained model.

* * * * *